US 6,599,890 B1

(12) United States Patent
McClure et al.

(10) Patent No.: US 6,599,890 B1
(45) Date of Patent: Jul. 29, 2003

(54) ARYLSULFONYL HYDROXAMIC ACID DERIVATIVES

(75) Inventors: Kim F. McClure, Mystic, CT (US); Mark C. Noe, Mystic, CT (US); Michael A. Letavic, Mystic, CT (US); Louis S. Chupak, Old Saybrook, CT (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/708,328

(22) Filed: Nov. 8, 2000

Related U.S. Application Data

(63) Continuation of application No. 09/125,055, filed as application No. PCT/IB98/00064 on Jan. 16, 1998.
(60) Provisional application No. 60/037,600, filed on Feb. 11, 1997.

(51) Int. Cl.[7] ..................... C07D 211/62; C07D 241/24; A61K 31/445
(52) U.S. Cl. ................. 514/183; 514/330; 514/354; 544/365; 546/225; 546/245; 546/323
(58) Field of Search ................. 546/225, 245, 546/323; 514/330, 354, 253.12; 544/365

(56) References Cited

U.S. PATENT DOCUMENTS 5,753,653 A    5/1998    Bender et al. ........... 514/227.5

FOREIGN PATENT DOCUMENTS

| EP | 606046 B1 | 7/1994 | ......... C07D/213/42 |
| EP | 935963 | * 8/1999 | |
| WO | 9633172 | 10/1996 | ......... C07D/211/96 |
| WO | 9808815 | 3/1998 | ......... C07D/207/48 |
| WO | 9808825 | 3/1998 | ......... C07D/241/04 |
| WO | WO 98/34918 | * 8/1998 | |

OTHER PUBLICATIONS

Sotrel et al., PubMed Abstract (Hum. Pathol. 31(10): 1274–98, Oct. 2000).*
Simone, Oncology: Introduction, Cecil Textbook of Medicine, 20th Edition, vol. 1, pp. 1004–1010, 1996.*

* cited by examiner

Primary Examiner—Deepak Rao
(74) Attorney, Agent, or Firm—Peter C. Richardson; Paul H. Ginsburg; Richard L. Catania

(57) ABSTRACT

A compound of the formula

I wherein $R^1$, $R^2$ $R^3$, $R^4$ $R^5$, $R^6$, $R^7$, $R^8$, $R^9$ and Q are as defined above, useful in the treatment of a condition selected from the group consisting of arthritis, cancer, tissue ulceration, macular degeneration, restenosis, periodontal disease, epidermolysis bullosa, scleritis, and other diseases characterized by matrix metalloproteinase activity, AIDS, sepsis, septic shock and other diseases involving the production of TNF. In addition, the compounds of the present invention may be used in combination therapy with standard non-steroidal anti-inflammatory drugs (NSAID'S) and analgesics, and in combination with cytotoxic drugs such as adriamycin, daunomycin, cis-platinum, etoposide, taxol, taxotere and other alkaloids, such as vincristine, in the treatment of cancer.

8 Claims, No Drawings

ARYLSULFONYL HYDROXAMIC ACID DERIVATIVES

The present application is a Continuation Application of U.S. patent application Ser. No. 09/125,055, filed Aug. 4, 1998 which was a 371 application of International Patent Application PCT/IB98/00064, filed Jan. 16, 1998 (which published as WO 98/34918), which claims benefit of U.S. Provisional Application 60/037,600, filed Feb. 11, 1997.

BACKGROUND OF THE INVENTION

The present invention relates to arylsulfonyl hydroxamic acid derivatives which are inhibitors of matrix metalloproteinases or the production of tumor necrosis factor (TNF) and as such are useful in the treatment of a condition selected from the group consisting of arthritis, cancer, tissue ulceration, restenosis, periodontal disease, epidermolysis bullosa, scleritis and other diseases characterized by matrix metalloproteinase activity, AIDS, sepsis, septic shock and other diseases involving the production of TNF. In addition, the compounds of the present invention may be used in combination therapy with standard non-steroidal anti-inflammatory drugs (hereinafter NSAID'S) and analgesics for the treatment of arthritis, and in combination with cytotoxic drugs such as adriamycin, daunomycin, cis-platinum, etoposide, taxol, taxotere and alkaloids, such as vincristine, in the treatment of cancer.

The invention also relates to a method of using such compounds in the treatment of the above diseases in mammals, especially humans, and to pharmaceutical compositions useful therefor.

There are a number of enzymes which effect the breakdown of structural proteins and which are structurally related metalloproteases. Matrix-degrading metalloproteinases, such as gelatinase, stromelysin and collagenase, are involved in tissue matrix degradation (e.g. collagen collapse) and have been implicated in many pathological conditions involving abnormal connective tissue and basement membrane matrix metabolism, such as arthritis (e.g. osteoarthritis and rheumatoid arthritis), tissue ulceration (e.g. corneal, epidermal and gastric ulceration), abnormal wound healing, periodontal disease, bone disease (e.g. Paget's disease and osteoporosis), tumor metastasis or invasion, as well as HIV-infection (*J. Leuk. Biol.*, 52 (2): 244–248, 1992).

Tumor necrosis factor is recognized to be involved in many infectious and auto-immune diseases (W. Fiers, *FEBS Letters*, 1991, 285, 199). Furthermore, it has been shown that TNF is the prime mediator of the inflammatory response seen in sepsis and septic shock (C. E. Spooner et al., *Clinical Immunology and Immunopathology*, 1992, 62 S11).

SUMMARY OF THE INVENTION

The present invention relates to a compound of the formula

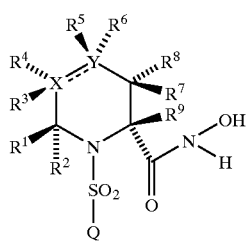

I or the pharmaceutically acceptable salt thereof, wherein the broken line represents an optional double bond;

X is carbon, oxygen, sulfur, SO, $SO_2$ or nitrogen;

Y is carbon, oxygen, sulfur, SO, $SO_2$ or nitrogen;

$R^1$, $R^2$, $R^3$, $R^4$ $R^5$, $R^6$, $R^7$, $R^8$ and $R^9$ are selected from the group consisting of hydrogen, hydroxy, ($C_1$—$C_6$)alkyl optionally substituted by one or two groups selected from ($C_1$—$C_6$)alkylthio, ($C_1$—$C_6$)alkoxy, trifluoromethyl, halo, ($C_6$—$C_{10}$)aryl, ($C_2$—$C_9$)heteroaryl, ($C_6$—$C_{10}$)arylamino, ($C_6$—$C_{10}$)arylthio, ($C_6$—$C_{10}$)aryloxy, ($C_2$—$C_9$)heteroarylamino, ($C_2$—$C_9$)heteroarylthio, ($C_2$—$C_9$)heteroaryloxy, ($C_6$—$C_{10}$)aryl($C_6$—$C_{10}$)aryl, ($C_3$—$C_6$)cycloalkyl, hydroxy, piperazinyl, ($C_6$—$C_{10}$)aryl($C_1$—$C_6$)alkoxy, ($C_2$—$C_9$)heteroaryl($C_1$—$C_6$)alkoxy, ($C_1$—$C_6$)acylamino, ($C_1$—$C_6$)acylthio, ($C_1$—$C_6$)acyloxy, ($C_1$—$C_6$)alkylsulfinyl, ($C_6$—$C_{10}$)arylsulfinyl, ($C_1$—$C_6$)alkylsulfonyl, ($C_6$—$C_{10}$)arylsulfonyl, amino, ($C_1$—$C_6$)alkylamino or (($C_1$—$C_6$)alkyl)$_2$amino; ($C_2$—$C_6$)alkenyl, ($C_6$—$C_{10}$)aryl($C_2$—$C_6$)alkenyl, ($C_2$—$C_9$)heteroaryl($C_2$—$C_6$)alkenyl, ($C_2$—$C_6$)alkynyl, ($C_6$—$C_{10}$)aryl($C_2$—$C_6$)alkynyl, ($C_2$—$C_9$)heteroaryl($C_2$—$C_6$)alkynyl, ($C_1$—$C_6$)alkylamino, ($C_1$—$C_6$)alkylthio, ($C_1$—$C_6$)alkoxy, perfluoro($C_1$—$C_6$)alkyl, ($C_6$—$C_{10}$)aryl, ($C_2$—$C_9$)heteroaryl, ($C_6$—$C_{10}$)arylamino, ($C_6$—$C_{10}$)arylthio, ($C_6$—$C_{10}$)aryloxy, ($C_2$—$C_9$)heteroarylamino, ($C_2$—$C_9$)heteroarylthio, ($C_2$—$C_9$)heteroaryloxy, ($C_3$—$C_6$)cycloalkyl, ($C_1$—$C_6$)alkyl(hydroxymethylene), piperidyl, ($C_1$—$C_6$)alkylpiperidyl, ($C_1$—$C_6$)acylamino, ($C_1$—$C_6$)acylthio, ($C_1$—$C_6$)acyloxy, $R^{10}$($C_1$—$C_6$)alkyl or a group of the formula

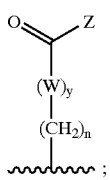

II wherein n is 0 to 6;

y is 0 or 1;

W is oxygen or >$NR^{24}$;

Z is —$OR^{11}$, —$NR^{24}R^{11}$, azetidinyl, pyrrolidinyl, piperidinyl, piperazinyl, morpholinyl, thiomorpholinyl, indolinyl, isoindolinyl, tetrahydroquinolinyl, tetrahydroisoquinolinyl or a bridged diazabicycloalyl ring selected from the group consisting of

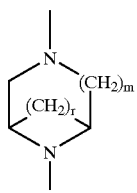

a

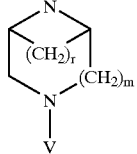

b

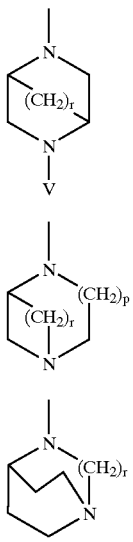

wherein r is 1, 2 or 3;

m is 1 or 2;

p is 0 or 1; and

V is hydrogen, $(C_1-C_3)$alkyl, $(C_1-C_6)$alkyl(C=O)—, $(C_1-C_6)$ alkoxy(C=O)—, $(C_6-C_{10})$aryl(C=O)—, $(C_6-C_{10})$aryloxy(C=O)—, $(C_6-C_{10})$aryl$(C_1-C_6)$alkyl(C=O)—, $(C_6-C_{10})$aryl-$(C_1-C_6)$alkoxy(C=O)—, or $(C_1-C_6)$alkoxy(C=O)—O—;

wherein each heterocyclic group (i.e., each Z cyclic group containing one or more heteroatoms) may optionally be independently substituted by one or two groups selected from hydroxy, $(C_1-C_6)$alkyl, $(C_1-C_6)$alkoxy, $C_1-C_{10}$acyl, $(C_1-C_{10})$acyloxy, $(C_6-C_{10})$aryl, $(C_2-C_9)$heteroaryl, $(C_6-C_{10})$aryl$(C_1-C_6)$alkyl, $(C_2-C_9)$heteroaryl$(C_1-C_6)$alkyl, hydroxy $(C_1-C_6)$alkyl, $(C_1-C_6)$alkoxy$(C_1-C_6)$alkyl, $(C_1-C_6)$acyloxy$(C_1-C_6)$alkyl, $(C_1-C_6)$alkylthio, $(C_1-C_6)$alkylthio$(C_1-C_6)$alkyl, $(C_6-C_{10})$arylthio, $(C_6-C_{10})$arylthio$(C_1-C_6)$alkyl, $R^{12}R^{13}N$—, $R^{12}R^{13}NSO_2$—, $R^{12}R^{13}N(C=O)$—, $R^{12}R^{13}N(C=O)—(C_1-C_6)$alkyl, $R^{14}SO_2$—, $R^{14}SO_2NH$—, $R^{15}(C=O)—[N(R^{12})]$—, $R^{16}O(C=O)$—, or $R^{16}O(C=O)—(C_1-C_6)$alkyl;

wherein $R^{10}$ is $(C_1-C_6)$acylpiperazinyl, $(C_6-C_{10})$arylpiperazinyl, $(C_2-C_9)$heteroarylpiperazinyl, $(C_1-C_6)$alkylpiperazinyl, $(C_6-C_{10})$aryl$(C_1-C_6)$alkylpiperazinyl, $(C_2-C_9)$heteroaryl$(C_1-C_6)$alkylpiperazinyl, morpholinyl, thiomorpholinyl, pyrrolidinyl, piperidyl, $(C_1-C_6)$alkylpiperidyl, $(C_6-C_{10})$arylpiperidyl, $(C_2-C_9)$heteroarylpiperidyl, $(C_1-C_6)$alkylpiperidyl$(C_1-C_6)$alkyl, $(C_6-C_{10})$arylpiperidyl$(C_1-C_6)$alkyl, $(C_2-C_9)$heteroarylpiperidyl-$(C_1-C_6)$alkyl or $(C_1-C_6)$acylpiperidyl;

$R^{11}$ is hydrogen, $(C_6-C_{10})$aryl, $(C_2-C_9)$heteroaryl, $(C_6-C_{10})$aryl$(C_1-C_6)$alkyl, $(C_2-C_9)$heteroaryl$(C_1-C_6)$alkyl, $(C_1-C_6)$alkyl$(C_6-C_{10})$aryl$(C_1-C_6)$alkyl$(C_2-C_9)$heteroaryl$(C_1-C_6)$alkyl, 5-indanyl, —CHR$^{17}$O—(C=O)—R$^{18}$ or —CH$_2$(C=O)—NR$^{19}$R$^{20}$;

$R^{12}$ and $R^{13}$ are each independently hydrogen, $(C_1-C_6)$alkyl, $(C_6-C_{10})$aryl, $C_2-C_9$heteroaryl, $(C_6-C_{10})$aryl$(C_1-C_6)$alkyl or $(C_2-C_9)$heteroaryl$(C_1-C_6)$alkyl or $R^{12}$ and $R^{13}$ may be taken together with the nitrogen to which they are attached to form an azetidinyl, pyrrolidinyl, piperidinyl, morpholinyl or thiomorpholinyl ring;

$R^{14}$ is trifluoromethyl, $(C_1-C_6)$alkyl, $(C_6-C_{10})$aryl, $(C_2-C_9)$heteroaryl, $(C_6-C_{10})$aryl$(C_1-C_6)$alkyl or $(C_2-C_9)$heteroaryl$(C_1-C_6)$alkyl;

$R^{15}$ is hydrogen, $(C_1-C_6)$alkyl, $(C_1-C_6)$alkoxy, $(C_6-C_{10})$aryl, $(C_2-C_9)$heteroaryl, $(C_1-C_6)$aryl$(C_1-C_6)$alkyl$(C_6-C_{10})$aryl$(C_1-C_6)$alkoxy or $(C_2-C_9)$heteroaryl$(C_1-C_6)$alkyl;

$R^{16}$ is $(C_1-C_6)$alkyl, $(C_6-C_{10})$aryl, $(C_2-C_9)$heteroaryl, $(C_6-C_{10})$aryl$(C_1-C_6)$alkyl, 5-indanyl, —[CH(R$^{17}$)]O—(C=O)—R$^{18}$, —CH$_2$(C=O)—NR$^{19}$R$^{20}$, or R$^{21}$O$(C_1-C_6)$alkyl;

$R^{17}$ is hydrogen or $(C_1-C_6)$alkyl;

$R^{18}$ is $(C_1-C_6)$alkyl, $(C_1-C_6)$alkoxy or $(C_6-C_{10})$aryl;

$R^{19}$ and $R^{20}$ are each independently hydrogen or $(C_1-C_6)$alkyl or may be taken together with the nitrogen to which they are attached to form an azetidinyl, pyrrolidinyl, piperidinyl, morpholinyl or thiomopholinyl ring;

$R^{21}$ is H$_2$N(CHR$^{22}$)(C=O)—;

$R^{22}$ is the side chain of a natural D- or L-amino acid;

$R^{23}$ is hydrogen, $(C_1-C_6)$acyl, $(C_1-C_6)$alkyl, $(C_6-C_{10})$aryl$(C_1-C_6)$alkyl, $(C_2-C_9)$heteroaryl$(C_1-C_6)$alkyl or $(C_1-C_6)$alkylsulfonyl;

$R^{24}$ wherever it occurs is independently hydrogen or $(C_1-C_6)$alkyl;

or $R^1$ and $R^2$, or $R^3$ and $R^4$, or $R^5$ and $R^6$ may be taken together to form a carbonyl;

or $R^1$ and $R^2$, or $R^3$ and $R^4$, or $R^5$ and $R^6$, or $R^7$ and $R^8$ may be taken together to form a $(C_3-C_6)$cycloalkyl, oxacyclohexyl, thiocyclohexyl, indanyl or tetralinyl ring or a group of the formula

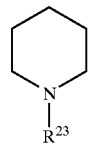

Q is $(C_1-C_{10})$alkyl, $(C_6-C_{10})$aryl, $(C_6-C_{10})$aryloxy$(C_6-C_{10})$aryl, $(C_6-C_{10})$aryl$(C_6-C_{10})$aryl, $(C_6-C_{10})$aryl$(C_6-C_{10})$aryl$(C_1-C_6)$alkyl, $(C_6-C_{10})$aryl$(C_1-C_6)$alkoxy$(C_1-C_6)$alkyl, $(C_6-C_{10})$aryloxy$(C_2-C_9)$heteroaryl, $(C_2-C_9)$heteroaryl, $(C_1-C_6)$alkyl$(C_6-C_{10})$aryl, $(C_1-C_6)$alkoxy$(C_6-C_{10})$aryl, $(C_6-C_{10})$aryl$(C_1-C_6)$alkoxy$(C_6-C_{10})$aryl, $(C_2-C_9)$heteroaryloxy$(C_6-C_{10})$aryl, $(C_1-C_6)$alkyl$(C_2-C_9)$heteroaryl, $(C_1-C_6)$alkoxy$(C_2-C_9)$heteroaryl, $(C_6-C_{10})$aryl$(C_1-C_6)$alkoxy$(C_2-C_9)$heteroaryl, $(C_2-C_9)$heteroaryloxy$(C_2-C_9)$heteroaryl, $(C_6-C_{10})$aryloxy$(C_1-C_6)$alkyl, $(C_2-C_9)$heteroaryloxy$(C_1-C_6)$alkyl, $(C_1-C_6)$alkyl$(C_6-C_{10})$aryloxy$(C_6-C_{10})$aryl, $(C_1-C_6)$alkyl$(C_2-C_9)$heteroaryloxy$(C_6-C_{10})$aryl, $(C_1-C_6)$alkyl$(C_6-C_{10})$aryloxy$(C_2-C_9)$heteroaryl, $(C_1-C_6)$alkoxy$(C_6-C_{10})$aryloxy$(C_6-C_{10})$aryl, $(C_1-C_6)$alkoxy$(C_2-C_9)$heteroaryloxy$(C_6-C_{10})$aryl or $C_1-C_6)$alkoxy$(C_6-C_{10})$aryloxy$(C_2-C_9)$heteroaryl optionally substituted by fluoro, chloro, $(C_1-C_6)$alkyl, $(C_1-C_6)$alkoxy or perfluoro$(C_1-C_3)$alkyl;

with the proviso that when y is zero, Q is other than $(C_6—C_{10})aryl(C_6—C_{10})aryl$, $(C_6—C_{10})aryl(C_1—C_6)$ alkoxy$(C_6—C_{10})aryl$ or $(C_6—C_{10})aryl(C_1—C_6)alkoxy$ $(C_2—C_9)heteroaryl$, and anyone of $R^1$–$R^9$ is a group of formula II then Z must be substituted when defined as azetidinyl, pyrrolidinyl, morpholinyl, thiomorpholinyl, indolinyl, isoindolinyl, tetrahydroquinolinyl, tetrahydroisoquinolinyl, piperazinyl, $(C_1—C_{10})$ acylpiperazinyl, $(C_1—C_6)alkylpiperazinyl$, $(C_6—C_{10})$ arylpiperazinyl, $(C_2—C_9)heteroarylpiperazinyl$ or a bridged diazabicycloalkyl ring;

with the proviso that when y is zero, Q is other than $(C_6—C_{10})aryl(C_6—C_{10})aryl$, $(C_6—C_{10})aryl(C_1—C_6)$ alkoxy$(C_6—C_{10})aryl$ or $(C_6—C_{10})aryl(C_1—C_6)alkoxy$ $(C_2—C_9)heteroaryl$, then at least one of $R^1, R^2, R^3, R^4, R^5, R^6, R^7, R^8$ and $R^9$ must be defined as the group of formula II;

with the proviso that when Q is $(C_6—C_{10})aryl(C_6—C_{10})$ aryl, $(C_6—C_{10})aryl(C_1—C_6)alkoxy(C_6—C_{10})aryl$ or $(C_6—C_{10})aryl(C_1—C_6)alkoxy(C_2—C_9)heteroaryl$, then $R^1$–$R^9$ may be other than formula II but when $R^1$, $R^2, R^3, R^4, R^5, R^6, R^7, R^8$, and $R^9$ are all defined by hydrogen or $(C_1—C_6)alkyl$, either X or Y is oxygen, sulfur, SO, —SO$_2$— or nitrogen, or the broken line represents a double bond;

with the proviso that $R^7$ is other than hydrogen only when $R^8$ is other than hydrogen;

with the proviso that $R^6$ is other than hydrogen only when $R^5$ is other than hydrogen;

with the proviso that $R^3$ is other than hydrogen only when $R^4$ is other than hydrogen;

with the proviso that $R^2$ is other than hydrogen only when $R^1$ is other than hydrogen;

with the proviso that when $R^1, R^2$ and $R^9$ are a substituent comprising a heteroatom, the heteroatom cannot be directly bonded to the 2- or 6-positions of the ring;

with the proviso that when X is nitrogen, $R^4$ is not present;

with the proviso that when X is oxygen, sulfur, SO, SO$_2$ or nitrogen and when one or more of the group consisting of $R^1, R^2, R^5$ and $R^6$, is a substituent comprising a heteroatom, the heteroatom cannot be directly bonded to the 4- or 6-positions;

with the proviso that when Y is oxygen, sulfur, SO, SO$_2$ or nitrogen and when one or more of the group consisting of $R^3, R^4, R^7$ and $R^8$, are independently a substituent comprising a heteroatom, the heteroatom cannot be directly bonded to the 3- or 5-positions;

with the proviso that when X is oxygen, sulfur, SO or SO$_2$, $R^3$ and $R^4$ are not present;

with the proviso that when y is 1 and W is $NR^{24}$ or oxygen, Z cannot be hydroxy;

with the proviso that when Y is oxygen, sulfur, SO or SO$_2$, $R^5$ and $R^6$ are not present;

with the proviso that when Y is nitrogen, $R^6$ is not present;

with the proviso that when the broken line represents a double bond, $R^4$ and $R^6$ are not present;

with the proviso that when $R^3$ and $R^5$ are independently a substituent comprising a heteroatom when the broken line represents a double bond, the heteroatom cannot be directly bonded to positions X and Y;

with the proviso that when either the X or Y position is oxygen, sulfur, SO, SO$_2$ or nitrogen, the other of X or Y is carbon;

with the proviso that when X or Y is defined by a heteroatom, the broken line does not represent a double bond.

The term "alkyl", as used herein, unless otherwise indicated, includes saturated monovalent hydrocarbon radicals having straight, branched or cyclic moieties or combinations thereof.

The term "alkoxy", as used herein, includes O-alkyl groups wherein "alkyl" is defined above.

The term "aryl", as used herein, unless otherwise indicated, includes an organic radical derived from an aromatic hydrocarbon by removal of one hydrogen, such as phenyl or naphthyl, optionally substituted by 1 to 3 substituents independently selected from the group consisting of fluoro, chloro, cyano, nitro, trifluoromethyl, $(C_1—C_6)$ alkoxy, $(C_6—C_{10})aryloxy$, trifluoromethoxy, difluoromethoxy and $(C_1—C_6)alkyl$.

The term "heteroaryl", as used herein, unless otherwise indicated, includes an organic radical derived from an aromatic heterocyclic compound by removal of one hydrogen, such as pyridyl, furyl, pyroyl, thienyl, isothiazolyl, imidazolyl, benzimidazolyl, tetrazolyl, pyrazinyl, pyrimidyl, quinolyl, isoquinolyl, benzofuryl, isobenzofuryl, benzothienyl, pyrazolyl, indolyl, isoindolyl, purinyl, carbazolyl, isoxazolyl, thiazolyl, oxazolyl, benzthiazolyl or benzoxazolyl, optionally substituted by 1 to 2 substituents independently selected from the group consisting of fluoro, chloro, trifluoromethyl, $(C_1—C_6)alkoxy$, $(C_6—C_{10})aryloxy$, trifluoromethoxy, difluoromethoxy and $(C_1—C_6)alkyl$.

The term "acyl", as used herein, unless otherwise indicated, includes a radical of the general formula RCO wherein R is alkyl, alkoxy (such as methyloxy carbonyl), aryl, arylalkyl or arylalkyloxy and the terms "alkyl" or "aryl" are as defined above.

The term "acyloxy", as used herein, includes O-acyl groups wherein "acyl" is defined above.

The term "D- or L-amino acid", as used herein, unless otherwise indicated, includes glycine, alanine, valine, leucine, isoleucine, phenylalanine, asparagine, glutamine, tryptophan, proline, serine, threonine, tyrosine, hydroxyproline, cysteine, cystine, methionine, aspartic acid, glutamic acid, lysine, arginine or histidine.

The positions on the ring of formula I, as used herein, are defined as follows:

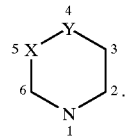

The preferred conformation of the compound of formula I includes hydroxamic acid axially disposed in the 2-position.

The compound of formula I may have chiral centers and therefore exist in different enantiomeric forms. This invention relates to all optical isomers and stereoisomers of the compounds of formula I and mixtures thereof.

Preferred compounds of formula I include those wherein Y- is carbon.

Other preferred compounds of formula I include those wherein Q is $(C_1—C_6)alkoxy(C_6—C_{10})aryl$, $(C_6—C_{10})aryl$ $(C_1—C_6)alkoxy(C_6—C_{10})aryl$, or $(C_6—C_{10})aryl(C_1—C_6)$ alkoxy$(C_1—C_6)alkyl$ wherein each terminal aryl group is optionally substituted by fluoro.

Other preferred compounds of formula I include those wherein $R^2, R^3, R^6, R^7$ and $R^9$ are hydrogen.

More preferred compounds of formula I include those wherein Y is carbon; Q is $(C_1—C_6)alkoxy(C_6—C_{10})aryl$, $(C_6—C_{10})aryl(C_1—C_6)alkoxy(C_6—C_{10})aryl$, or $(C_6—C_{10})$ aryl$(C_1—C_6)alkoxy(C_1—C_6)alkyl$.

Specific preferred compounds of formula I include the following:

(2R,4R)-1-[4-(4-Fluorobenzyloxy)-benzenesulfonyl]-2-hydroxycarbamoyl-piperidine-4-carboxylic acid;

(2R,4R)-1-[4-(4-Fluorobenzyloxy)-benzenesulfonyl]-2-hydroxycarbamoly-piperidine-4-carboxylic acid methyl ester;

(2R,4R)-1-[3-(4-Fluorophenoxy)-propane-1-sulfonyl]-2-hydroxycarbamoyl-piperidine-4-carboxylic acid;

(2R,4R)-1-[3-(4-Fluorophenoxy)-propane-1-sulfonyl]-2-hydroxycarbamoyl-piperidine-4-carboxylic acid methyl ester;

(2R,3S)-{1-[4-(4-Fluorobenzyloxy)-benzenesulfonyl]-2-hydroxycarbamoyl-piperidin-3-yl}-carbamic acid isopropyl ester;

3-(S)-4-(4'-Fluorobiphenyl-4-sulfonyl)-2,2-dimethyl-thiomorpholine-3-carboxylic acid hydroxyamide;

3-(S)-4-[4-(4-Fluorobenzyloxy)benzenesulfonyl]-2,2-dimethyl-thiomorpholine-3-carboxylic acid hydroxyamide;

(2R,4S)-1-[4-(4-Fluorobenzyloxy)-benzenesulfonyl]-4-hydroxy-piperidine-2-carboxylic acid hydroxyamide; and (2R,4R)-1-(4-Methoxybenzenesulfonyl)-4-(piperazine-1-carbonyl)-piperidine-2-carboxylic acid hydroxyamide hydrochloride.

Other compounds of the invention include:

(3S)-4-[4-(2-Chloro-thiazol-5-ylmethoxy)-benzenesulfonyl]-2,2-dimethyl-thiomorpholine-3-carboxylic acid hydroxyamide;

(3S)-2,2-Dimethyl-4-[4-(thiazol-5-ylmethoxy)-benzenesulfonyl]-thiomorpholine-3-carboxylic acid hydroxyamide;

(3S)-2,2-Dimethyl-4-[4-(pyridin-4-ylmethoxy)-benzenesulfonyl]-thiomorpholine-3-carboxylic acid hydroxyamide;

(3S)-4-{4-[2-(4-Fluorophenyl)-ethoxy]-benzenesulfonyl}-2,2-dimethyl-thiomorpholine-3-carboxylic acid hydroxyamide;

(3S)-2,2-Dimethyl-4-[4-(2-pyridin-4-yl-ethoxy)-benzenesulfonyl]-thiomorpholine-3-carboxylic acid hydroxyamide;

(3S)-4-[4-(Benzothiazol-2-ylmethoxy)-benzenesulfonyl]-2,2-dimethyl-thiomorpholine-3-carboxylic acid hydroxyamide;

(3S)-2,2-Dimethyl-4-[4-(5-trifluoromethyl-benzothiazol-2-ylmethoxy)-benzenesulfonyl]-thiomorpholine-3-carboxylic acid hydroxyamide;

(3S)-2,2-Dimethyl-4-[4-(1H-tetrazol-5-ylmethoxy)-benzenesulfonyl]thiomorpholine-3-carboxylic acid hydroxyamide;

(2R,3S)-{1-[4-(2-Chloro-thiazol-5-ylmethoxy)-benzenesulfonyl]-2-hydroxycarbamoyl-piperidin-3-yl}-carbamic acid methyl ester;

(2R,3S)-{2-Hydroxycarbamoyl-1-[4-(thiazol-5-ylmethoxy)-benzenesulfonyl]-piperidin-3-yl}-carbamic acid methyl ester;

(2R,3S)-{2-Hydroxycarbamoyl-1-[4-(pyridin-4-ylmethoxy)-benzenesulfonyl]-piperidine-3-yl}-carbamic acid methyl ester;

(2R,3S)-{1-[4-(4-Fluorobenzyloxy)-benzenesulfonyl]-2-hydroxycarbamoyl-piperidine-3-yl}-carbamic acid methyl ester;

(2R,3S)-(1-{4-[2-(4-Fluorophenyl)-ethoxy]-benzenesulfonyl}-2-hydroxycarbamoyl-piperidin-3-yl)-carbamic acid methyl ester;

(2R,3S)-{2-Hydroxycarbamoyl-1-[4-(2-pyridin-4-yl-ethoxy)-benzenesulfonyl]-piperidin-3-yl}-carbamic acid methyl ester;

(2R,3S)-{1-[4-(Benzothiazol-2-ylmethoxy)-benzenesulfonyl]-2-hydroxycarbamoyl-piperidin-3-yl}-carbamic acid methyl ester;

(2R,3S)-{2-Hydroxycarbamoly-1-[4-(5-trifluoromethyl-benzothiazol-2-ylmethoxy)-benzenesulfonyl]-piperidin-3-yl}-carbamic acid methyl ester;

(2R,3S)-{2-Hydroxycarbamoyl-1-[4-(1H-tetrazol-5-ylmethoxy)-benzenesulfonyl]-piperidin-3-yl}-carbamic acid methyl ester;

(2R,3S)-1-[4-(2-Chloro-thiazol-5-ylmethoxy)-benzenesulfonyl]-3-hydroxy-piperidine-2-carboxylic acid hydroxyamide;

(2R,3S)-3-Hydroxy-1-[4-(thiazol-5-ylmethoxy)-benzenesulfonyl]-piperidine-2-carboxylic acid hydroxyamide;

(2R,3S)-3-Hydroxy-1-[4-(pyridin-4-ylmethoxy)-benzene-sulfonyl]-piperidine-2-carboxylic acid hydroxyamide;

(2R,3S)-1-[4-(4-Fluorobenzyloxy)-benzenesulfonyl]-3-hydroxy-piperidine-2-carboxylic acid hydroxyamide;

(2R,3S)-1-{4-[2-(4-Fluorophenyl)-ethoxy]-benzenesulfonyl}-3-hydroxy-piperidine-2-carboxylic acid hydroxyamide;

(2R,3S)-3-Hydroxy-1-[4-(2-pyridin-4-yl-ethoxy)-benzenesulfonyl]-piperidine-2-carboxylic acid hydroxyamide;

(2R,3S)-1-[4-(Benzothiazol-2-ylmethoxy)-benzenesulfonyl]-3-hydroxy-piperidine-2-carboxylic acid hydroxyamide;

(2R,3S)-3-Hydroxy-1-[4-(5-trifluoromethyl-benzothiazol2-ylmethoxy)-benzenesulfonyl]-piperidine-2-carboxylic acid hydroxyamide;

(2R,3S)-3-Hydroxy-1-[4-(1H-tetrazol-5-ylmethoxy)-benzenesulfonyl]-piperi-dine-2-carboxylic acid hydroxyamide;

(2R,3S)-1-[4-(2-Chloro-thiazol-5-ylmethoxy)-benzenesulfonyl]-3-hydroxy-3-methyl-piperidine-2-carboxylic acid hydroxyamide;

(2R,3S)3-Hydroxy-3-methyl-1-[4-(thiazol-5-ylmethoxy)-benzenesulfonyl]-piperidine-2-carboxylic acid hydroxyamide;

(2R,3S)-3-Hydroxy-3-methyl-1-[4-(pyridin-4-ylmethoxy)benzenesulfonyl]-piperidine-2-carboxylic acid hydroxyamide;

(2R,3S)-1-[4-(4-Fluorobenzyloxy)-benzenesulfonyl]-3-hydroxy-3-methyl-piperidine-2-carboxylic acid hydroxyamide;

(2R,3S)-1-{4-[2-(4-Fluorophenyl)-ethoxy]-benzenesulfonyl}-3-hydroxy-3-methyl-piperidine-2-carboxylic acid hydroxyamide;

(2R,3S)-3-Hydroxy-3-methyl-1-[4-(2-pyridin-4-yl-ethoxy)-benzenesulfonyl]-piperidine-2-carboxylic acid hydroxyamide;

(2R,3S)-1-[4-(Benzothiazol-2-ylmethoxy)-benzenesulfonyl]-3-hydroxy-3-methyl-piperidine-2-carboxylic acid hydroxyamide;

(2R,3S)-3-Hydroxy-3-methyl-1-[4-(5-trifluoromethyl-benzothiazol-2-ylmethoxy)-benzenesulfonyl]-piperidine-2-carboxylic acid hydroxyamide;

(2R,3S)-3-Hydroxy-3-methyl-1-[4-(1H-tetrazol-5-yl-methoxy)-benzenesulfonyl]-piperidine-2-carboxylic acid hydroxyamide;

(3R)-4-[4-(2-Chloro-thiazol-5-ylmethoxy)-benzenesulfonyl]-2,2-dimethyl-morpholine-3-carboxylic acid hydroxyamide;

(3R)-2,2-Dimethyl-4-[4-(thiazol-5-ylmethoxy)-benzenesulfonyl]-morpholine-3-carboxylic acid hydroxyamide;

(3R)-2,2-Dimethyl-4-[4-(pyridin-4-ylmethoxy)-benzenesulfonyl]-morpholine-3-carboxylic acid hydroxyamide;

(3R)-4-[4-(4-Fluorobenzyloxy)-benzenesulfonyl]-2,2-dimethyl-morpholine-3-carboxylic acid hydroxyamide;

(3R)-4-{4-[2-(4-Fluorophenyl)-ethoxy]-benzenesulfonyl}-2,2-dimethyl-morpholine-3-carboxylic acid hydroxyamide;

(3R)-2,2-Dimethyl-4-[4-(2-pyridin-4-yl-ethoxy)-benzenesulfonyl]-morpholine-3-carboxylic acid hydroxyamide;

(3R)-4-[4-(Benzothiazol-2-ylmethoxy)-benzenesulfonyl]-2,2-dimethyl-morpholine-3-carboxylic acid hydroxyamide;

(3R)-2,2-Dimethyl-4-[4-(5-trifluoromethyl-benzothiazol-2-ylmethoxy)-benzenesulfonyl]-morpholine-3-carboxylic acid hydroxyamide;

(3R)-2,2-Dimethyl-4-[4-(1H-tetrazol-5-ylmethoxy)-benzenesulfonyl]-morpholine-3-carboxylic acid hydroxyamide;

(2R,4R)-1-[4-(2-Chloro-thiazol-5-ylmethoxy)-benzenesulfonyl]-2-hydroxycarbamoyl-piperidine-4-carboxylic acid;

(2R,4R)-2-Hydroxycarbamoyl-1-[4-(thiazol-5-ylmethoxy)-benzenesulfonyl]-piperidine-4-carboxylic acid;

(2R,4R)-2-Hydroxycarbamoyl-1-[4-(pyridin-4-ylmethoxy)-benzenesulfonyl]-piperidine-4-carboxylic acid;

(2R,4R)-1-{4-[2-(4-Fluorophenyl)-ethoxy]-benzenesulfonyl}-2-hydroxycarbamoyl-piperidine-4-carboxylic acid;

(2R,4R)-2-Hydroxycarbamoyl-1-[4-(2-pyridin-4-yl-ethoxy)-benzenesulfonyl]-piperidine-4-carboxylic acid;

(2R,4R)-1-[4-(Benzothiazol-2-ylmethoxy)-benzenesulfonyl]-2-hydroxycarbamoyl-piperidine-4-carboxylic acid;

(2R,4R)-2-Hydroxycarbamoyl-1-[4-(5-trifluoromethyl-benzothiazol-2-ylmethoxy)-benzenesulfonyl]-piperidine-4-piperidine-4-carboxylic acid;

(2R,4R)-2-Hydroxycarbamoyl-1-[4-(1H-tetrazol-5-yl-methoxy)-benzenesulfonyl]-piperidine-4-carboxylic acid;

(3R)-4-[4-(2-Chloro-thiazol-5-ylmethoxy)-benzenesulfonyl]-3-methyl-morpholine-3-carboxylic acid hydroxyamide;

(3R)-3-Methyl-4-[4-(thiazol-5-ylmethoxy)-benzenesulfonyl]-morpholine-3-carboxylic acid hydroxyamide;

(3R)-3-Methyl-4-[4-(pyridin-4-ylmethoxy)-benzenesulfonyl]-morpholine-3-carboxylic acid hydroxyamide;

(3R)-4-[4-(4-Fluorobenzyloxy)-benzenesulfonyl]-3-methyl-morpholine-3-carboxylic acid hydroxyamide;

(3R)-4-{4-[2-(4-Fluorophenyl)-ethoxy]-benzenesulfonyl}-3-methyl-morpholine-3-carboxylic acid hydroxyamide;

(3R)-3-Methyl-4-[4-(2-pyridin-4-yl-ethoxy)-benzenesulfonyl]-morpholine-3-carboxylic acid hydroxyamide;

(3R)-4-[4-(Benzothiazol-2-ylmethoxy)-benzenesulfonyl]-3-methyl-morpholine-3-carboxylic acid hydroxyamide;

(3R)-3-Methyl-4-[4-(5-trifluoromethyl-benzothiazol-2-ylmethoxy)-benzenesulfonyl]-morpholine-3-carboxylic acid hydroxyamide;

(3R)-3-Methyl-4-[4-(1H-tetrazol-5-ylmethoxy)-benzenesulfonyl]-morpholine-3-carboxylic acid hydroxyamide;

(2R)-1-[4-(2-Chloro-thiazol-5-ylmethoxy)-benzenesulfonyl]-2-methyl-3-oxo-piperidine-2-carboxylic acid hydroxyamide;

(2R)-2-Methyl-3-oxo-1-[4-(thiazol-5-ylmethoxy)-benzenesulfonyl]-piperidine-2-carboxylic acid hydroxyamide;

(2R)-2-Methyl-3-oxo-1-[4-(pyridin-4-ylmethoxy)-benzenesulfonyl]-piperidine-2-carboxylic acid hydroxyamide;

(2R)-1-[4-(4-Fluorobenzyloxy)-benzenesulfonyl]-2-methyl-3-oxo-piperidine-2-carboxylic acid hydroxyamide;

(2R)-1-{4-[2-(4-Fluorophenyl)-ethoxy]-benzenesulfonyl}-2-methyl-3-oxo-piperidine-2-carboxylic acid hydroxyamide;

(2R)-2-Methyl-3-oxo-1-[4-(2-pyridin-4-yl-ethoxy)-benzenesulfonyl]-piperidine-2-carboxylic acid hydroxyamide;

(2R)-1-[4-(Benzothiazol-2-ylmethoxy)-benzenesulfonyl]-2-methyl-3-oxo-piperidine-2-carboxylic acid hydroxyamide;

(2R)-2-Methyl-3-oxo-1-[4-(5-trifluoromethyl-benzothiazol-2-ylmethoxy)-benzenesulfonyl]-piperidine-2-carboxylic acid hydroxyamide;

(2R)-2-Methyl-3-oxo-1-[4-(1H-tetrazol-5-ylmethoxy)-benzenesulfonyl]-piperidine-2-carboxylic acid hydroxyamide;

(2R,4S)-1-(4-Benzyloxy-benzenesulfonyl)-4-butylaminomethyl-4-hydroxy-piperidine-2-carboxylic acid hydroxyamide;

(2R,4S)-4-Butylaminomethyl-1-[4-(4-fluorobenzyloxy)-benzenesulfonyl]-4-hydroxy-piperidine-2-carboxylic acid hydroxyamide;

(2R,4S)-4-Benzylamino-1-(4-benzyloxy-benzenesulfonyl)-piperidine-2-carboxylic acid hydroxyamide;

(2R,4S)-4-Benzylamino-1-[4-(4-fluorobenzyloxy)-benzenesulfonyl]-piperidine-2-carboxylic acid hydroxyamide;

(2R)-1-[4-(4-Fluorobenzyloxy)-benzenesulfonyl]-4-oxo-piperidine-2-carboxylic acid hydroxyamide;

(2R,4R)-1-(4-Benzyloxy-benzenesulfonyl)-4-hydroxy-piperidine-2-carboxylic acid hydroxyamide;

(2R,4R)-1-[4-(4-Fluorobenzyloxy)-benzenesulfonyl]-4-hydroxy-piperidine-2-carboxylic acid hydroxyamide;

(2R)-1-[4-(4-Fluorobenzyloxy)-benzenesulfonyl]-4-methyl-piperazine-2-carboxylic acid hydroxyamide;

(2R,5S)-1-[4-(4-Fluorobenzyloxy)-benzenesulfonyl]-5-hydroxy-piperidine-2-carboxylic acid hydroxyamide;

(2R,5S)-1-(4-Benzyloxy-benzenesulfonyl)-5-hydroxy-piperidine-2-carboxylic acid hydroxyamide;

(2R,5R)-1-(4-Benzyloxy-benzenesulfonyl)-5-hydroxy-piperidine-2-carboxylic acid hydroxyamide;

(2R,5R)-1-[4-(4-Fluorobenzyloxy)-benzenesulfonyl]-5-hydroxy-piperidine-2-carboxylic acid hydroxyamide;

(2R,3S)-1-(4-Benzyloxy-benzenesulfonyl)-3-hydroxy-piperidine-2-carboxylic acid hydroxyamide;

(2R,4S)-1-(4-Benzyloxy-benzenesulfonyl)-4-hydroxy-piperidine-2-carboxylic acid hydroxyamide;

(2R,4S)-1-[4-(4-Fluorobenzyloxy)-benzenesulfonyl]-4-hydroxy-piperidine-2-carboxylic acid hydroxyamide;

1-(4-Butoxy-benzenesulfonyl)-3-(morpholine-4-carbonyl)-piperidine-2-carboxylic acid hydroxyamide;

1-[4-(4-Fluoro-benzyloxy)-benzenesulfonyl)-3-(morpholine-4-carbonyl)-piperidine-2-carboxylic acid hydroxyamide;

1-[3-(Fluoro-benzyloxy)-propane-1-sulfonyl]-3-(morpholine-4-carbonyl)-piperidine-2-carboxylic acid hydroxymide;

1-(4-Butoxy-benzenesulfonyl)-3-(pyrrolidine-1-carbonyl)-piperidine-2-carboxylic acid hydroxyamide;

1-[4-(4-Fluoro-benzyloxy)-benzyloxy)-benzenesulfonyl)-3-(pyrrolidine-1-carbonyl)-piperidine-2-carboxylic acid hydroxyamide;

1-[3-(4-Fluoro-benzyloxy)-propane-1-sulfonyl)-3-(pyrrolidine-1-carbonyl)-piperidine-2-carboxylic acid hydroxyamide; and 1-[4-(4-Fluoro-benzyloxy)-benzenesulfonyl]-2-hydroxycarbamoyl-piperidine-4-carboxylic acid.

The present invention also relates to a pharmaceutical composition for (a) the treatment of a condition selected from the group consisting of arthritis, cancer, synergy with cytotoxic anticancer agents, tissue ulceration, macular degeneration, restenosis, periodontal disease, epidermolysis bullosa, scleritis, in combination with standard NSAID'S and analgesics and other diseases characterized by matrix metalloproteinase activity, AIDS, sepsis, septic shock and other diseases involving the production of tumor necrosis factor (TNF) or (b) the inhibition of matrix metalloproteinases or the production of tumor necrosis factor (TNF) in a mammal, including a human, comprising an amount of a compound of formula I or a pharmaceutically acceptable salt thereof effective in such treatments and a pharmaceutically acceptable carrier.

The present invention also relates to a method for the inhibition of (a) matrix metalloproteinases or (b) the production of tumor necrosis factor (TNF) in a mammal, including a human, comprising administering to said mammal an effective amount of a compound of formula I or a pharmaceutically acceptable salt thereof.

The present invention also relates to a method for treating a condition selected from the group consisting of arthritis, cancer, tissue ulceration, macular degeneration, restenosis, periodontal disease, epidermolysis bullosa, scleritis, compounds of formula I may be used in combination with standard NSAID'S and analgesics and in combination with cytotoxic anticancer agents, and other diseases characterized by matrix metalloproteinase activity, AIDS, sepsis, septic shock and other diseases involving the production of tumor necrosis factor (TNF) in a mammal, including a human, comprising administering to said mammal an amount of a compound of formula I or a pharmaceutically acceptable salt thereof effective in treating such a condition.

DETAILED DESCRIPTION OF THE INVENTION

The following reaction Schemes illustrate the preparation of the compounds of the present invention. Unless otherwise indicated $R^1$, $R^2$, $R^3$, $R^4$, $R^5$, $R^6$, $R^7$, $R^8$, $R^9$, n and Ar in the reaction Schemes and the discussion that follow are defined as above.

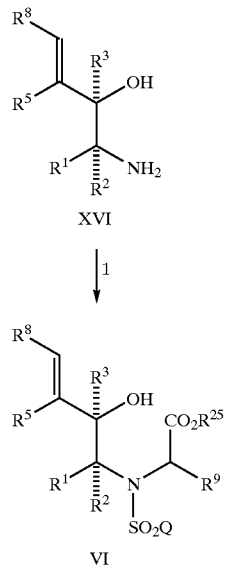

Preparation 1

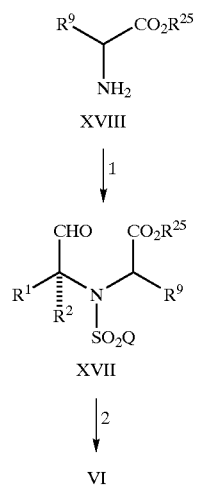

Preparation 2

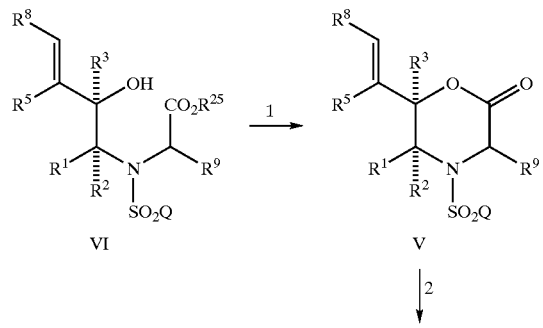

Scheme 1

-continued
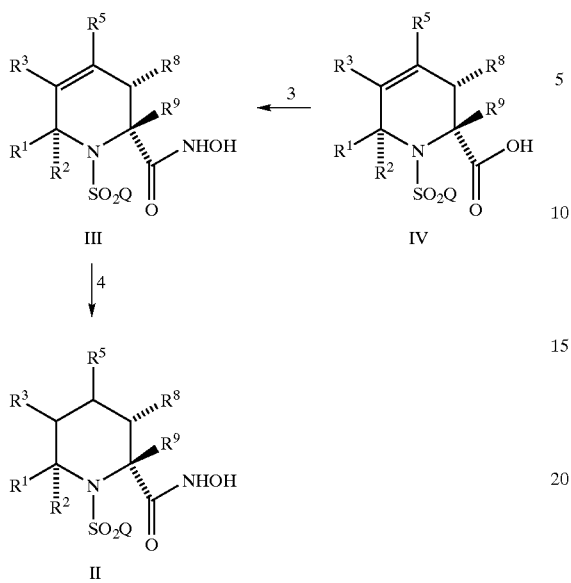
Scheme 2
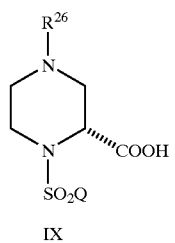
IX
↓ 1
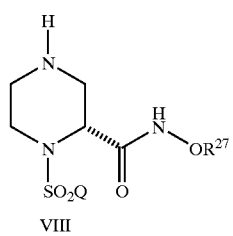
VIII
↓ 2
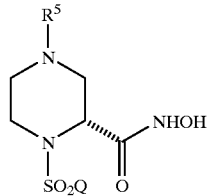
VII
Scheme 3
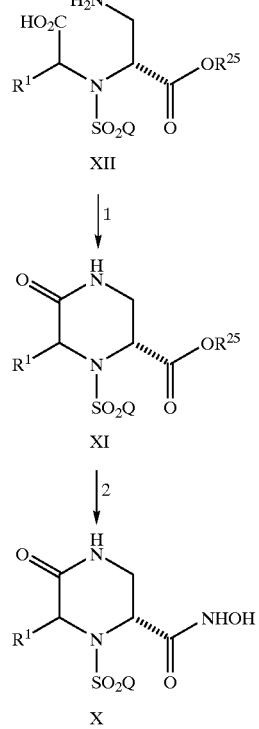
Scheme 4
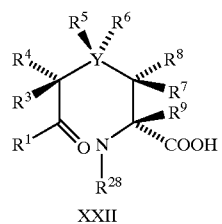
XXII
↓ 1
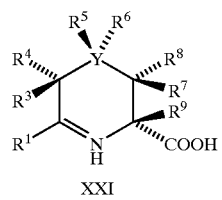
XXI
↓ 2
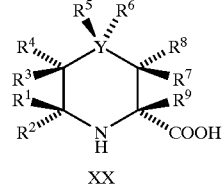
XX
↓ 3

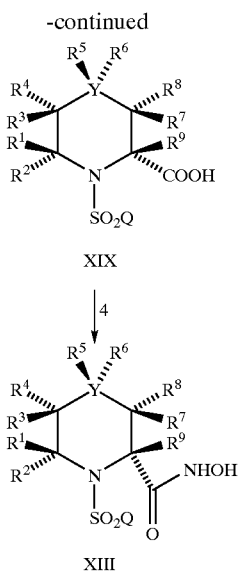

XIX

↓ 4

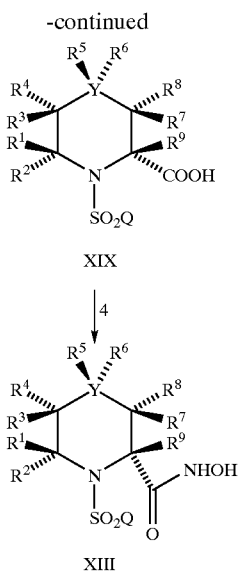

XIII

Scheme 5

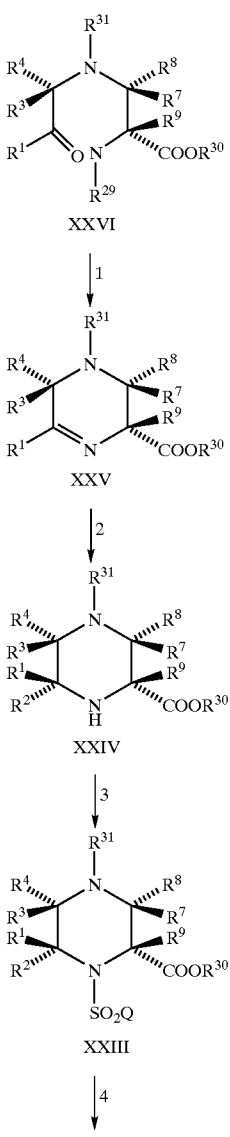

XXVI

↓ 1

XXV

↓ 2

XXIV

↓ 3

XXIII

↓ 4

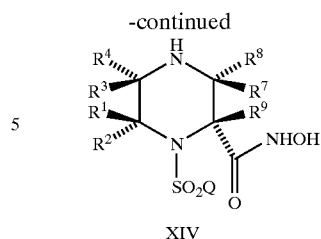

XIV

Preparation 1 refers to the preparation of intermediates of the formula VI. Compounds of the formula VI are converted to compounds of the formula I according to the methods of Scheme 1. The starting materials of formula XVI can be prepared according to methods well known to those of ordinary skill in the art.

In reaction 1 of Preparation 1, the compound of formula XVI is converted to the corresponding hydroxy ester compound of formula VI by first reacting XVI with an arylsulfonylhalide in the presence of triethylamine and an aprotic solvent, such as methylene chloride, tetrahydrofuran or dioxane, at a temperature between about 20° C. to about 30° C., preferably at room temperature. The compound so formed is further reacted with a compound of the formula

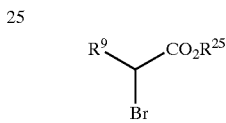

wherein $R^{25}$ is carbobenzyloxy, $(C_1–C_6)$alkyl, benzyl, allyl or tert-butyl, in the presence of sodium hexamethyldisilazane and a tetrahydrofuran-dimethylformamide solvent mixture at a temperature between about –20° C. to about 20° C., preferably about 0° C., to form the hydroxy ester compound of formula VI.

Preparation 2 refers to an alternate method of preparing compounds of the formula VI. The starting materials of formula XVIII can be prepared according to methods well known to those of ordinary skill in the art. In reaction 2 of Preparation 2, the amine compound of formula XVIII, wherein $R^{25}$ is as defined above, is converted to the corresponding arylsulfonyl amine compound of formula XVII by (1) reacting XVIII with an arylsulfonylhalide in the presence of triethylamine and an aprotic solvent, such as methylene chloride, tetrahydrofuran, or dioxane, at a temperature between about 20° C. to about 30° C., preferably at room temperature, (2) reacting the compound so formed with a compound of the formula

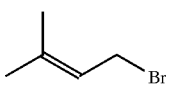

in the presence of sodium hexamethyldisilazane and a tetrahydrofuran-dimethylformamide solvent mixture at a temperature between about –20° C. to about 20° C., preferably about 0° C., and (3) further reacting the compound so formed with ozone in a methylene chloride-methanol solution at a temperature between about –90° C. to about –70° C., preferably about –78° C. The unstable ozonide compound so formed is then reacted with triphenylphosphine to form the arylsulfonyl amine compound formula XVII. In Reaction 2 of Preparation 2, the arylsulfonyl amine compound of formula XVII is converted to the corresponding hydroxy ester compound of formula VI by reacting XVII with a compound of the formula

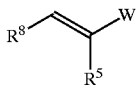

wherein W is lithium, magnesium, copper or chromium.

Scheme 1 refers to the preparation of compounds of the formula II, which are compounds of the formula I, wherein X and Y are carbon; $R^4$, $R^6$ and $R^7$ are hydrogen; and the dashed line between X and Y is absent. In reaction 1 of Scheme 1, the compound of formula VI, wherein the $R^{25}$ protecting group is carbobenzyloxy, ($C_1$–$C_6$) alkyl, benzyl, allyl or tert-butyl, is converted to the corresponding morpholinone compound of formula V by lactonization and subsequent Claisen rearrangement of the compound of formula VI. The reaction is facilitated by the removal of the $R^{25}$ protecting group from the compound of formula VI and is carried out under conditions appropriate for that particular $R^{25}$ protecting group in use. Such conditions include: (a) treatment with hydrogen and a hydrogenation catalyst, such as 10% palladium on carbon, where $R^{25}$ is carbobenzyloxy, (b) saponification where $R^{25}$ is lower alkyl, (c) hydrogenolysis where $R^{25}$ is benzyl, (d) treatment with a strong acid, such as trifluoroacetic acid or hydrochloric acid, where $R^{25}$ is tert-butyl, or (e) treatment with tributyltinhydride and acetic acid in the presence of catalytic bis(triphenylphosphine) palladium (II) chloride where $R^{25}$ is allyl.

In reaction 2 of Scheme 1, the morpholinone compound of formula V is converted to the carboxylic acid compound of formula IV by reacting V with lithium hexamethyldisilazane in an aprotic solvent, such as tetrahydrofuran, at a temperature between about –90° C. to about –70° C., preferably about –78° C. Trimethylsilyl chloride is then added to the reaction mixture and the solvent, tetrahydrofuran, is removed in vacuo and replaced with toluene. The resulting reaction mixture is heated to a temperature between about 100° C. to about 120° C., preferably about 110° C., and treated with hydrochloric acid to form the carboxylic acid compound of formula IV.

In reaction 3 of Scheme 1, the carboxylic acid compound of formula IV is converted to the corresponding hydroxamic acid compound of formula III by treating IV with 1-(3-dimethylaminopropyl)-3-ethylcarbodiimide and 1-hydroxybenztriazole in a polar solvent, such as dimethylformamide, followed by the addition of hydroxylamine to the reaction mixture after a time period between about 15 minutes to about 1 hour, preferably about 30 minutes. The hydroxylamine is preferably generated in situ from a salt form, such as hydroxylamine hydrochloride, in the presence of a base, such as N-methylmorpholine. Alternatively, a protected derivative of hydroxylamine or its salt form, where the hydroxyl group is protected as a tert-butyl, benzyl or allyl ether, may be used in the presence of (benzotriazol-1-yloxy)tris(dimethylamino) phosphonium hexafluorphosphate and a base, such as N-methylmorpholine. Removal of the hydroxylamine protecting group is carried out by hydrogenolysis for a benzyl protecting group or treatment with a strong acid, such as trifluoroacetic acid, for a tert-butyl protecting group. The allyl protecting group may be removed by treatment with tributyltinhydride and acetic acid in the presence of catalytic bis(triphenylphosphine) palladium (II) chloride. N,O-bis(4-methoxybenzyl)hydroxylamine may also be used as the protected hydroxylamine derivative where deprotection is achieved using a mixture of methanesulfonic acid and trifluoroacetic acid.

In reaction 4 of Scheme 1, the hydroxamic acid compound of formula III is converted, if desired, to the corresponding piperidine compound of formula II by treating III with hydrogen and a hydrogenation catalyst, such a 10% palladium on carbon.

Scheme 2 refers to the preparation of compounds of the formula VII, which are compound of the formula I wherein Y is nitrogen; X is carbon; $R^1$, $R^2$, $R^3$, $R^4$, $R^7$ and $R^8$ are hydrogen, and $R^6$ is absent. The starting materials of formula IX can be prepared according to methods well known to those of ordinary skill in the art. In reaction 1 of Scheme 2, the arylsulfonylpiperazine compound of formula IX, wherein $R^{26}$ is carbobenzyloxy, benzyl or carbotertbutyloxy, is converted to the compound of formula VIII by reacting IX with a protected derivative of hydroxylamine of the formula

$R^{27}OHN_2.HCl$ wherein $R^{27}$ is tertbutyl, benzyl or allyl, in the presence of dicylohexylcarbodiimide, dimethylaminopyridine and an aprotic solvent, such as methylene chloride. The $R^{26}$ protecting group is chosen such that it may be selectively removed in the presence of an without loss of the $R^{27}$ protecting group, therefore, $R^{26}$ cannot be the same as $R^{27}$. Removal of the $R^{26}$ protecting group from the compound of formula IX is carried out under conditions appropriate for that particular $R^{26}$ protecting group in use. Such conditions include; (a) treatment with a hydrogen and a hydrogenation catalyst, such as 10% palladium on carbon, where $R^{26}$ is carbobenzyloxy, (b) hydrogenolysis where $R^{26}$ is benzyl or (c) treatment with a strong acid, such as trifluoroacetic acid or hydrochloric acid where $R^{26}$ is carbotertbutyloxy.

In reaction 2 of Scheme 2, the compound of formula VIII is converted to the corresponding hydroxamic acid compound of formula VII, wherein $R^5$ is hydrogen or ($C_1$–$C_6$) alkyl, by reacting, if desired, VIII with an alkylhalide when $R^5$ is ($C_1$–$C_6$)alkyl. Subsequent removal of the $R^{27}$ hydroxylamine protecting group is carried out by hydrogenolysis for a benzyl protecting group or treatment with a strong acid, such as trifluoroacetic acid, for a tert-butyl protecting group. The allyl protecting group may be removed by treatment with tributyltinhydride and acetic acid in the presence of catalytic bis(triphenylphosphine) palladium (II) chloride.

Scheme 3 refers to the preparation of compounds of the formula X, which are compounds of the formula I wherein Y is nitrogen; X is carbon; $R^2$, $R^7$, $R^8$ and $R^9$ are hydrogen; $R^3$ and $R^4$ taken together are carbonyl; $R^5$ is hydrogen, and $R^6$ is absent. In reaction 1 of Scheme 3, the arylsulfonylamine compound of formula XII, wherein $R^{26}$ is as defined above, is converted to the corresponding piperazine compound of formula XI by reacting XII with a carbodiimide and a base, such as triethylamine. The compound of formula XI is further reacted to give the hydroxamic acid compound of formula X according to the procedure described above in reaction 3 of Scheme 1.

Scheme 4 refers to the preparation of compounds of the formula XIII. The starting materials of formula XVIII can be prepared according to methods well known to those of ordinary skill in the art. Compounds of the formula XIII are compounds of the formula I wherein X is carbon, and the dotted line between X and Y is absent. In reaction 1 of Scheme 4, removal of the $R^{26}$ protecting group and subsequent reductive amination of the compound of formula XXII, wherein Y is oxygen, sulfur or carbon, to give the corresponding imine compound of formula XXI is carried out under conditions appropriate for that particular $R^{26}$ protecting group in use. Such conditions include those used above for removal of the $R^{26}$ protecting group in reaction 1 of Scheme 2.

In reaction 2 of Scheme 4, the imine compound of formula XXI is converted to the corresponding piperidine compound of formula XX by reacting XXI with a nucleophile of the formula $R^2M$ wherein M is lithium, magnesium halide or cerium halide. The reaction is carried out in ether solvents, such as diethyl ether or tetrahydrofuran, at a temperature between about $-78°$ C. to about $0°$ C., preferably about $-70°$ C.

In reaction 3 of Scheme 4, the sulfonation of the piperidine compound of formula XX to given the corresponding arylsulfonylpiperidine compound of formula XIX is carried out by reacting XX with an arylsulfonylhalide in the presence of triethylamine and an aprotic solvent, such as methylene chloride, tetrahydrofuran or dioxane, at a temperature between about $20°$ C. to about $30°$ C., preferably at room temperature.

In reaction 4 of Scheme 4, the arylsulfonylpiperidine compound of formula XIX is converted to the hydroxamic acid compound of formula XIII according to the procedure described above in reaction 3 of Scheme 1.

Scheme 5 refers to the preparation of compounds of the formula XIV, which are compounds of formula I wherein Y is nitrogen, X is carbon, the dotted line between X and Y is absent, $R^5$ is hydrogen and $R^6$ is absent. In reaction 1 of Scheme 5, the compound of formula XXVI, wherein the $R^{29}$ and $R^{31}$ protecting groups are each independently selected from the group consisting of carbobenzyloxy, benzyl and carbotertbutyloxy and $R^{30}$ is carbobenzyloxy, $(C_1-C_6)$alkyl, benzyl, allyl or tert-butyl, is converted to the corresponding imine compound of formula XXV by the removal of the $R^{29}$ protecting group and subsequent reductive amination of the compound of formula XXVI. The $R^{29}$ protecting group is chosen such that it may be selectively removed in the presence of and without loss of $R^{31}$ protecting group. Removal of the $R^{29}$ protecting group from the compound of formula XXVI is carried out under conditions appropriate for that particular $R^{29}$ protecting group in use which will not affect the $R^{31}$ protecting group. Such conditions include; (a) treatment with hydrogen and a hydrogenation catalyst, such as 10% palladium on carbon, where $R^{29}$ is carbobenzyloxy and $R^{31}$ is tert-butyl, (b) saponification where $R^{29}$ is $(C_1-C_6)$ alkyl and $R^{31}$ is tert-butyl, (c) hydrogenolysis where $R^{29}$ is benzyl and $R^{31}$ is $(C_1-C_6)$ alkyl or tert-butyl, (d) treatment with a strong acid such as trifluoracetic acid or hydrochloric acid where $R^{29}$ is tert-butyl and $R^{31}$ is $(C_1-C_6)$alkyl, benzyl or allyl, or (e) treatment with tributyltinhydride and acetic acid in the presence of catalytic bis(triphenylphosphine) palladium (II) chloride where $R^{29}$ is allyl and $R^{31}$ is $(C_1-C_6)$ alkyl, benzyl or tert-butyl. The $R^{30}$ protective group may be selected such that it is removed in the same reaction step as the $R^{29}$ protecting group.

In reaction 2 of Scheme 5, the imine compound of formula XXV is converted to the corresponding compound of formula XXIV by reacting XXV with a nucleophile of the formula $R^2M$ wherein M is lithium, magnesium halide or calcium halide. The reaction is carried out in ether solvents, such as diethyl ether or tetrahydrofuran, at a temperature between about $-78°$ C. to about $0°$ C., preferably about $-70°$ C.

In reaction 3 of Scheme 5, the sulfonation of the piperidine compound of formula XXIV to give the corresponding arylsulfonylpiperidine compound of formula III is carried out according to the procedure described above in reaction 3 of Scheme 4.

In reaction 4 of Scheme 5, the arylsulfonylpiperidine compound of formula XXIII is converted to the hydroxamic acid compound of formula XIV by (1) removing the $R^{30}$, if needed, and $R^{31}$ protecting groups from XXIII followed by (2) reacting XXIII according to the procedure described above in reaction 3 of Scheme 1. Removal of the $R^{30}$ and $R^{31}$ protecting groups from the compound of formula XXIII is carried out under conditions appropriate for that particular $R^{30}$ and $R^{31}$ protecting group in use. Such conditions include those used above for removal of the $R^{25}$ protecting group in reaction 1 of Scheme 1.

Pharmaceutically acceptable salts of the acidic compounds of the invention are salts formed with bases, namely cationic salts such as alkali and alkaline earth metal salts, such as sodium, lithium, potassium, calcium, magnesium, as well as ammonium slats, such as ammonium, trimethylammonium, diethylammonium, and tris(hydroxymethyl)-methylammonium salts.

Similarly acid addition salts, such as of mineral acids, organic carboxylic and organic sulfonic acids e.g. hydrochloric acid, methanesulfonic acid, maleic acid, are also possible provided a basic group, such as pyridyl, constitutes part of the structure.

The ability of the compounds of formula I or their pharmaceutically acceptable salts (the compounds of the invention) to inhibit matrix metalloproteinases or the production of tumor necrosis factor (TNF) and, consequently, demonstrate their effectiveness for treating diseases characterized by matrix metalloproteinase or the production of tumor necrosis factor is shown by the following in vitro assay tests.

Biological Assay

Inhibition of Human Collagenase (MMP-1)

Human recombinant collagenase is activated with trypsin using the following ratio: 10 $\mu$g trypsin per 100 $\mu$g of collagenase. The trypsin and collagenase are incubated at room temperature for 10 minutes then a five fold excess (50 $\mu$g/10 $\mu$g trypsin) of soybean trypsin inhibitor is added.

10 mM stock solutions of inhibitors are made up in dimethyl sulfoxide and then diluted using the following Scheme:

10 mM→120 $\mu$M→12 $\mu$M→1.2 $\mu$M→0.12 $\mu$M

Twenty-five microliters of each concentration is then added in triplicate to appropriate wells of a 96 wells microfluor plate. The final concentration of inhibitor will be a 1:4 dilution after addition of enzyme and substrate. Positive controls (enzyme, no inhibitor) are set up in wells D1–D6 and blanks (no enzyme, no inhibitors) are set in wells D7–D12.

Collagenase is diluted to 400 ng/ml and 25 $\mu$l is then added to appropriate wells of the microfluor plate. Final concentration of collagenase in the assay is 100 ng/ml.

Substrate (DNP-Pro-Cha-Gly-Cys(Me)-His-Ala-Lys (NMA)-$NH_2$) is made as a 5 mM stock in dimethyl sulfoxide and then diluted to 20 $\mu$M in assay buffer. The assay is initiated by the addition of 50 $\mu$l substrate per well of the microfluor plate to give a final concentration of 10 $\mu$M.

Fluorescence readings (360 nM excitation, 460 nm emission) were taken at time 0 and then at 20 minute intervals. The assay is conducted at room temperature with a typical assay time of 3 hours.

Fluorescence vs time is then plotted for both the blank and collagnease containing samples (data from triplicate determinations is averaged). A time point that provides a good signal (the blank) and that is on a linear part of the curve (usually around 120 minutes) is chosen to determine $IC_{50}$ values. The zero time is used as a blank for each compound at each concentration and these values are subtracted from the 120 minute data. Data is plotted as inhibitor concentration vs % control (inhibitor fluorescence divided by fluorescence of collagenase alone×100). $IC_{50}$'s are determined from the concentration of inhibitor that gives a signal that is 50% of the control.

If $IC_{50}$'s are reported to be <0.03 µM then the inhibitors are assayed at concentrations of 0.3 µM, 0.03 µM and 0.003 µM.

Inhibitor of Gelatinase (MMP-2)

Inhibition of gelatinase activity is assayed using the Dnp-Pro-Cha-Gly-Cys(Me)-His-Ala-Lys(NMA)-NH$_2$ substrate (10 µM) under the same conditions as inhibition of human collagenase (MMP-1).

72 kD gelatinase is activated with 1 mM APMA (p-aminophenyl mercuric acetate) for 15 hours at 4° C. and is diluted to give a final concentration in the assay of 100 mg/ml. Inhibitors are diluted as for inhibition of human collagenase (MMP-1) to give final concentrations in the assay of 30 µM, 3 µM, 0.3 µM and 0.03 µM. Each concentration is done in triplicate.

Fluorescence readings (360 nm excitation, 460 emission) are taken at time zero and then at 20 minutes intervals for 4 hours.

$IC_{50}$'s are determined as per inhibition of human collagenase (MMP-1). If $IC_{50}$'s are reported to be less than 0.03 µM, then the inhibitors are assayed at final concentrations of 0.3 µM, 0.03 µM, 0.003 µM and 0.003 µM.

Inhibition of Stromelysin Activity (MMP-3)

Inhibition of stromelysin activity is based on a modified spectrophotometric assay described by Weingarten and Feder (Weingarten, H. and Feder, J., Spectrophotometric Assay for Vertebrate Collagenase, Anal. Biochem. 147, 437–440 (1985)). Hydrolysis of the thio peptolide substrate [Ac-Pro-Leu-Gly-SCH[CH$_2$CH(CH$_3$)$_2$]CO-Leu-Gly-OC$_2$H$_5$] yields a mercaptan fragment that can be monitored in the presence of Ellman's reagent.

Human recombinant prostromelysin is activated with trypsin using a ratio of 1 µl of a 10 mg/ml trypsin stock per 26 µg of stromelysin. The trypsin and stromelysin are incubated at 37° C. for 15 minutes followed by 10 µl of 10 mg/ml soybean trypsin inhibitor for 10 minutes at 37° C. for 10 minutes at 37° C. to quench trypsin activity.

Assays are conducted in a total volume of 250 µl of assay buffer (200 mM sodium chloride, 50 mM MES, and 10 mM calcium chloride, pH 6.0) in 96-well microliter plates. Activated stromelysin is diluted in assay buffer to 25 µg/ml. Ellman's reagent (3-Carboxy-4-nitrophenyl disulfide) is made as a 1M stock in dimethyl formamide and diluted to 5 mM in assay buffer with 50 µl per well yielding at 1 mM final concentration.

10 mM stock solutions of inhibitors are made in dimethyl sulfoxide and diluted serially in assay buffer such that addition of 50 µL to the appropriate wells yields final concentrations of 3 µM, 0.3 µM, 0.003 µM, and 0.0003 µM. All conditions are completed in triplicate.

A 300 mM dimethyl sulfoxide stock solution of the peptide substrate is diluted to 15 mM in assay buffer and the assay is initiated by addition of 50 µl to each well to give a final concentration of 3 mM substrate. Blanks consist of the peptide substrate and Ellman's reagent without the enzyme. Product formation was monitored at 405 nm with a Molecular Devices UVmax plate reader.

$IC_{50}$ values were determined in the same manner as for collagenase.

Inhibition of MMP-13

Human recombinant MMP-13 is activated with 2 mM APMA (p-aminophenyl mercuric acetate) for 1.5 hours, at 37° C. and is diluted to 400 mg/ml in assay buffer (50 mM Tris, pH 7.5, 200 mM sodium chloride, 5 mM calcium chloride, 20 µM zinc chloride, 0.02% brij). Twenty-five microliters and diluted enzyme is added per well of a 96 well microfluor plate. The enzyme is then diluted in a 1:4 ratio in the assay by the addition of inhibitor and substrate to give a final concentration in the assay of 100 mg/ml.

10 mM stock solution of inhibitors are made up in dimethyl sulfoxide and then diluted in assay buffer as per the inhibitor dilution scheme for inhibition of human collagenase (MMP-1): Twenty-five microliters of each concentration is added in triplicate to the microfluor plate. The final concentrations in the assay are 30 µM, 3 µM, 0.3 µM, and 0.03 µM.

Substrate (Dnp-Pro-Cha-Gly-Cys(Me)-His-Ala-Lys (NMA)-NH$_3$) is prepared as for inhibition of human collagenase (MMP-1) and 50 µl is added to each well to give a final assay concentration of 10 µM. Fluorescence readings (360 nM excitation; 450 emission) are taken at time 0 and every 5 minutes for 1 hour.

Positive controls consist of enzyme and substrate with no inhibitor and blanks consist of substrate only.

$IC_{50}$'s are determined as per inhibition of human collagenase (MMP-1). If $IC_{50}$'s are reported to be less than 0.03 µM, inhibitors are then assayed at final concentrations of 0.3 µM, 0.03 µM, 0.003 µM and 0.0003 µM.

Inhibition of TNF Production

The ability of the compounds or the pharmaceutically acceptable salts thereof to inhibit the production of TNF and, consequently, demonstrate their effectiveness for treating diseases involving the production of TNF is shown by the following in vitro assay:

Human mononuclear cells were isolated from anti-coagulated human blood using a one-step Ficoll-hypaque separation technique, (2) The mononuclear cells were washed three times in Hanks balanced salt solution (HBSS) with divalent cations and resuspended to a density of 2×10$^6$/ml in HBSS containing 1% BSA. Differential counts determined using the Abbott Cell Dyn 3500 analyzer indicated that monocytes ranged from 17 to 24% of the total cells in these preparations.

180µ of the cell suspension was allquoted into flate bottom 96 well plates (Costar). Additions of compounds and LPS (100 ng/ml final concentration) gave a final volume of 200 µl. All conditions were performed in triplicate. After a four hour incubation at 37° C. in an humidified CO$_2$ incubator, plates were removed and centrifuged (10 minutes at approximately 250×g) and the supernatants removed and assayed for TNFα using the R&D ELISA Kit.

For administration to mammals, including humans, for the inhibition of matrix metalloproteinases or the production of tumor necrosis factor (TNF), a variety of conventional routes may be used including orally, parenterally and topically. In general, the compounds of the invention will be administered orally or parenterally at dosages between about 0.1 and 25 mg/kg body weight of the subject to be treated per day, preferably from about 0.3 to 5 mg/kg. However, some variation in dosage will necessarily occur depending on the condition of the subject being treated. The person responsible for administration will, in any event, determine the appropriate dose for the individual subject.

The compounds of the invention can be administered in a wide variety of different dosage forms. In general, the therapeutically effective compounds of this invention are present in such dosage forms at concentration level ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelation and acacia. Additionally, lubricating agents such as magnesium stearate, sodium lauryl sulfate and talc are often very useful for tabletting purposes. Solid compositions of a similar type may also be employed as fillers in gelatin capsules; performed materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof. In the case of animals, they are advantageously contained in an animal feed or drinking water in a concentration of 5–5000 ppm, preferably 25 to 500 ppm.

For parenteral administration (intramuscular, intraperitoneal, subcutaneous and intravenous use) a sterile injectable solution of the active ingredient is usually prepared. Solutions of a therapeutic compound of the present invention in either sesame or peanut oil or in aqueous propylene glycol may be employed. The aqueous solutions should be suitably adjusted and buffered, preferably at a pH of greater than 8, if necessary and the liquid diluent first rendered isotonic. These aqueous solutions are suitable intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art. In the case of animals, compounds can be administered intramuscularly or subcutaneously at dosage levels of about 0.1 to 50 mg/kg/day, advantageously 0.2 to 10 mg/kg/day given in a single dose or up to 3 divided doses.

The present invention is illustrated by the following examples, but it is not limited to the details thereof.

EXAMPLE 1

(2R, 4R)-1-(4-Methoxy-benzenesulfonyl)-4-(piperazine-1-carbonyl)-piperidine-2-carboxylic acid hydroxyamide hydrochloride (a) To a stirred, cold (−78° C.) solution of (2R)-2-benzyloxycarbonylamino-pentanedioic acid 1-tert-butyl ester 5-methyl ester (5.6 g, 15.9 mmol), prepared as described in J. Org. Chem., 55, 1711–1721 (1990) and J. Med. Chem., 39, 73–85 (1996), in 30 mL of tetrahydrofuran was added lithium bis(trimethylsilyl)amide (40 mL, 1 M in tetrahydrofuran, 39.8 mmol). The resulting mixture was stirred for 1 hour at −45° C. and then recooled to −78° C. Allyl bromide (5.2 mL, 63.7 mmol) was then added. After 2 hours the reaction was quenched by the addition of 1 M aqueous hydrogen chloride at −78° C. The mixture was then extracted with diethyl ether. The combined ethereal extracts were washed with brine and the mixture was dried over sodium sulfate. After filtration and concentration of the filtrate, the crude product was purified by silica gel chromatography (elution with 1:5 ethyl acetate/hexanes) to provide (2R,4R)-4-allyl-2-benzyloxycarbonylamino-pentanedioic acid 1-tert-butyl ester 5-methyl ester.

(b) Ozone gas was bubbled through a stirred, cold, (−78° C.) solution of (2R,4R)-4-allyl-2-benzyloxycarbonylamino-pentanedioic acid 1-tert-butyl ester 5-methyl ester (5.0 g, 12.8 mmol) in 100 mL of 10:1 methanol/methylene chloride, and 0.73 mL of acetic acid until a blue color persisted. Nitrogen gas was then bubbled through the solution until the blue color dissipated. The mixture was warmed to ambient temperature and dimethyl sulfide (2.8 mL, 3.83 mmol) was added. The mixture was stirred for 48 hours, diluted with methylene chloride, and washed with 10% aqueous sodium carbonate, brine, and the mixture was dried over sodium sulfate. Filtration and concentration of the filtrate provided (2R,4S)-6-methoxy-piperidine-1,2,4-tricarboxylic acid 1-benzyl ester 2-tert-butyl ester 4-methyl ester as a clear oil, which was used in the subsequent step without purification.

(c) A mixture of (2R,4S)-6-methoxy-piperidine-1,2,4-tricarboxylic acid 1-benzyl ester 2-tert-butyl ester 4-methyl ester (4.85 g, 11.9 mmol) and 10% palladium on carbon (500 mg) in 100 mL of ethanol was shaken under a 45 psi atmosphere of hydrogen gas for 1.5 hours. The mixture was filtered through nylon and the filtrate was concentrated to provide (2R,4R)-piperidine-2,4-dicarboxylic acid 2-tert-butyl ester 4-methyl ester as light yellow oil, which was used in the subsequent step without further purification.

(d) To a stirred, cold (0° C.) solution of (2R,4R)-piperidine-2,4-dicarboxylic acid 2-tert-butyl ester 4-methyl ester (2.7 g, 11.1 mmol) and triethylamine (4.6 ml, 33.3 mmol) in 30 mL of methylene chloride was added 4-methoxy-benzenesulfonyl chloride (2.3 g, 11.1 mmol). The mixture was warmed to ambient temperature and stirred for 4 hours. The reaction was quenched by the addition of aqueous ammonium chloride and the mixture was extracted with ethyl acetate. The combined organic extracts were washed with brine, and the organic mixture was dried over sodium sulfate. After filtration and concentration of the filtrate, the resulting crude product was purified by silica gel chromatography (elution with 3:8 ethyl acetate/hexanes) to provide (2R,4R)-1-(4-methoxy-benzenesulfonyl)-piperidine-2,4-dicarboxylic acid 2-tert-butyl ester 4-methyl ester.

(e) To a stirred, cold (0° C.) solution of (2R,4R)-1-(4-methoxy-benzenesulfonyl)-piperidine-2,4-dicarboxylic acid 2-tert-butyl ester 4-methyl ester (4.4 g, 10.6 mmol) in 30 mL of methylene chloride was added 10 mL of trifluoroacetic acid dropwise. The mixture was stirred for 1 hour at 0° C. and for 8 hours at ambient temperature. Concentration provided (2R,4R)-1-(4-methoxy-benzenesulfonyl)-piperidine-2,4-dicarboxylic acid 4-methyl ester, which was used in the subsequent step without purification.

(f) To a stirred solution of (2R,4R)-1-(4-methoxy-benzenesulfonyl)-piperidine-2,4-dicarboxylic acid 4-methyl ester (4.4 g, 12.3 mmol), O-benzylhydroxylamine hydrochloride (2.15 g, 13.5 mmol), and triethylamine (5.15 mL, 36.9 mmol) was added benzotriazol-1-yloxy-tris(dimethylamino)phosphonium hexafluorophosphate (6.0 g, 12.3 mmol) at ambient temperature. The resulting mixture was stirred for 24 hours. The mixture was diluted with ethyl acetate and washed with 1 M aqueous hydrogen chloride, aqueous sodium bicarbonate, and brine. The organic mixture was dried over magnesium sulfate, filtered, and the filtrate was concentrated. The crude residue was purified by silica gel chromatography (elution with 5% methanol in methylene chloride) to provide (2R,4R)-2-benzyloxycarbamoyl-1-(4-methoxy-benzenesulfonyl)-piperidine-4-carboxylic acid methyl ester as a colorless solid.

(g) To a stirred cold (0° C.) solution of (2R,4R)-2-benzyloxycarbamoyl-1-(4-methoxy-benzenesulfonyl)-piperidine-4-carboxylic acid methyl ester (4.0 g, 8.6 mmol) in 10 mL of 9:1 methanol/water was added lithium hydroxide monohydrate (1.8 g, 43 mmol). The mixture was stirred for 2 hours before Amberlite IR-120 resin (96 g) was added. After 15 minutes, the mixture was filtered and the filtrate was concentrated to give (2R,4R)-2-benzyloxycarbamoyl-1-(4-methoxy-benzenesulfonyl)-piperidine-4-carboxylicacid, which was used in the subsequent reaction without purification.

(h) To a stirred solution of (2R,4R)-2-benzyloxycarbamoyl-1-(4-methoxy-benzenesulfonyl)-piperidine-4-carboxylic acid (500 mg, 1.11 mmol), tert-butyloxycarbonyl piperazine (226 mg, 1.21 mmol), and triethylamine (0.47 mL, 3.33 mmol) was added benzotriazol-1-yloxy-tris(dimethylamino)phosphonium hexafluorophosphate (535 mg, 1.21 mmol) at ambient temperature. The resulting mixture was stirred for 24 hours. The mixture was diluted with ethyl acetate and washed with 1 M aqueous hydrogen chloride, aqueous sodium bicarbonate, and brine. The organic mixture was dried over magnesium sulfate, filtered, and the filtrate was concentrated. The crude residue was purified by silica gel chromatography (elution with 2% methanol in methylene chloride) to provide (2R,4)-4-[2-benzyloxycarbamoyl-1-(4-methoxy-benzenesulfonyl)-piperidine-4-carbonyl]-piperizine-1-carboxylic acid tert-butyl ester as a colorless solid.

(i) A mixture of (2R,4R)-4-[2-benzyloxycarbamoyl-1-(4-methoxy-benzene-sulfonyl)-piperidine-4-carbonyl]-piperazine-1-carboxylic acid tert-butyl ester (500 mg, 0.81 mmol) and 5% palladium on barium sulfate (250 mg) in 10 mL of methanol was shaken under a 40 psi atmosphere of hydrogen gas for 1.5 hours. Filtration through nylon and concentration of the filtrate provided (2R,4R)-4-[2-hydroxycarbamoyl-1-(4-methoxy-benzenesulfonyl)-piperidine-4-carbonyl]-piperazine-1-carboxylic acid tert-butyl ester as a colorless solid, which was used in the subsequent step without purification.

(j) Hydrogen chloride gas was bubbled through a cold (0° C.) solution of (2R,4R)-4-[2-hydroxycarbamoyl-1-(4-methoxy-benzenesulfonyl)-piperidine-4-carbonyl]-piperazine-1-carboxylic acid tert-butyl ester (420 mg, 0.8 mmol) for 10 minutes. After an additional 20 minutes the mixture was concentrated to provide (2R, 4R)-1-(4-methoxy-benzenesulfonyl)-4-(piperazine-1-carbonyl)-piperidine-2-carboxylic acid hydroxyamide hydrochloride as a colorless solid: Mass spectrum (atmospheric pressure chemical ionization; basic mode) m/z (M+H) 427, 366; $^1$H NMR (dimethyl sulfoxide-$d_6$, 400 MHz, ppm) δ 10.70 (bd, 1 H, J=2.7 Hz), 9.06 (bs, 2 H), 8.84 (bs, 1 H), 7.70 (dd, 2 H, J=8.9, 2.9 Hz), 7.06 (dd, 2 H, J=8.9, 2.9 Hz); 4.42 (bs, 1 H), 3.80 (s, 3 H), 3.80–3.20 (m, 6 H), 3.04 (m, 4 H), 2.76 (m, 1 H), 1.79 (bd, 1 H, J=13.5 Hz), 1.52 (bd, 1 H, J=12.6 Hz), 1.32 (m, 1 H), 1.14 (m, 1H).

EXAMPLE 2

(2R,4R)-1-[3-(4-Fluorophenoxy)-propane-1-sulfonyl]-2-hydroxycarbamoyl-piperidine-4-carboxylic acid methyl ester (a) To a stirred solution of (2R,4R)-piperidine-2,4-dicarboxylic acid 2-tert-butyl ester 4-methyl ester (920 mg, 3.78 mmol) and triethylamine (1.58 ml, 11.3 mmol) in 10 mL of methylene chloride was added a solution of 3-(4-fluorophenoxy)-propane-1-sulfonyl chloride (1.05 g, 4.16 mmol) in 2 mL of methylene chloride under a nitrogen atmosphere. The mixture was stirred for 16 hours at ambient temperature (22° C.), then diluted with 20 mL of 1 N hydrochloric acid and 20 mL of methylene chloride. The organic layer was removed and washed with brine and dried over sodium sulfate. Filtration and concentration of the filtrate gave 2.8 g of a yellow oil, which was purified by flash chromatography (3:2 hexanes/ethyl acetate elution) to give 1.15 g (2R,4R)-1-[3-(4-fluoro-phenoxy)-propane-1-sulfonyl]-piperidine-2,4-dicarboxylic acid 2-tert-butyl ester 4-methyl ester of as a yellow oil.

(b) To a stirred, cold (0° C.) solution of (2R,4R)-1-[3-(4-fluorophenoxy)-propane-1-sulfonyl]-piperidine-2,4-dicarboxylic acid 2-tert-butyl ester 4-methyl ester (1.15 g, 2.5 mmol) in 10 mL of methylene chloride was added 10 mL of trifluoracetic acid. The mixture was allowed warm to ambient temperature (22° C.) over 16 hours. The mixture was concentrated in vacuo to give 970 mg of crude (2R, 4R)-1-[3-(4-fluorophenoxy)-propane-1-sulfonyl]-piperidine-2,4-dicarboxylic acid 4-methyl ester as a orange solid.

(c) To a stirred solution of (2R,4R)-1-[3-(4-fluorophenoxy)-propane-1-sulfonyl]-piperidine-2,4-dicarboxylic acid 4-methyl ester (970 mg, 2.4 mmol) in 5 mL of methylene chloride was added triethylamine (1.0 mL, 7.2 mmol) and O-benzylhydroxylamine hydrochloride (410 mg, 2.64 mmol) at ambient temperature (22° C.) To the resulting solution was added benzotriazol-1-yloxy-tris(dimethylamino)phosphonium hexafluorophosphate (1.17 g, 2.64 mmol) and the mixture was stirred for 16 hours under a nitrogen atmosphere. The mixture was diluted with 25 mL of 1 N hydrochloric acid and 25 mL of ethyl acetate. The organic layer was removed and the aqueous layer was extracted with ethyl acetate (2×). The combined organic layers were washed with saturated aqueous sodium carbonate (1×) and brine (1×). The organic layer was dried (sodium sulfate), filtered, and the filtrate was concentrated in vacuo. Purification of the viscous yellow residue by flash chromatography (eluting with 1:1 ethyl acetate/hexanes) gave 810 mg of (2R,4R)-2-benzyloxycarbamoyl-1-[3-(4-fluorophenoxy)-propane-1-sulfonyl]-piperidine-4-carboxylic acid methyl ester as a clear oil.

(d) A mixture of (2R,4R)-2-benzyloxycarbamoyl-1-[3-(4-fluorophenoxy)-propane-1-sulfonyl]-piperidine-4-carboxylic acid methyl ester (800 mg, 1.57 mmol) and 200 mg of 5% palladium on barium sulfate in 15 mL of methanol was shaken in a Parr apparatus under a 40 psi hydrogen gas atmosphere for 2 hours. The catalyst was removed by passage of the mixture through a 0.45 μm nylon filter and the filtrate was concentrated to give 650 mg of (2R,4R)-1-[3-(4-fluorophenoxy)-propane-1-sulfonyl]-2-hydroxycarbamoyl-piperidine-4-carboxylic acid methyl ester as a white foam: MS (atmospheric pressure chemical ionization) acidic mode, 417 (M−1); $^1$H NMR (400 MHz, CDCl$_3$) δ 6.94–6.97 (m, 2 H), 6.80–6.83 (m, 2 H), 4.56 (s, 1 H), 4.03 (t, 2 H, J=5.3 Hz), 3.83 (d, 1 H, J=12.9 Hz), 3.68 (s, 3 H), 3.15–3.28 (m, 3 H), 2.76 (t, 1 H, J=11.5 Hz), 2.54 (d, 1 H, J=13.5 Hz), 2.26 (d, 2 H, J=5.9 Hz), 2.02 (m, 1 H, J=13.0 Hz), 1.73–1.78 (m, 1 H), 1.56–1.62 (m, 1 H).

EXAMPLE 3

(2R,4R)-1-[3-(4-Fluorophenoxy)-propane-1-sulfonyl]-2-hydroxycarbamoyl-piperidine-4-carboxylic acid To a stirred, cold (0° C.) solution of (2R,4R)-1-[3-(4-fluorophenoxy)-propane-1-sulfonyl]-2-hydroxycarbamoylpiperidine-4-carboxylic acid methyl ester (400 mg, 0.96 mmol) in 5 mL of a methanol/water mixture (10:1) was added lithium hydroxide monohydrate (120 mg, 2.88 mmol). After 3 hours at 0° C., prerinsed (methanol) Amberlite resin (4.1 g) was added. The mixture was filtered and the filtrate was concentrated to give 370 mg of (2R,4R)-1-[3-(4-fluorophenoxy)-propane-1-sulfonyl]-2-hydroxycarbamoyl-piperidine-4-carboxylic acid as a white foam: MS (atmospheric pressure chemical ionization) acidic mode, 403 (M−1).

EXAMPLE 4

(2R,4R)-1-[4-(4-Fluorobenzyloxy)-benzenesulfonyl]-2-hydroxycarbamoyl-piperidine-4-carboxylic acid methyl ester 4-(4-Fluoro-benzyloxy)-benzenesulfonyl chloride. MS: 465 (M−1).

The titled compound of example 4 was prepared by a method analogous to that described in example 2 using the reagents.

EXAMPLE 5

(2R,4R)-1-[4-(4-Fluorobenzyloxy)-benzenesulfonyl]-2-hydroxycarbamoyl-piperidine-4-carboxylic acid. MS: 451 (M−1).

The titled compound of example 5 was prepared by a method analogous to that described in example 3 starting with 1-[4-(4-Fluoro-benzyloxy)-benzenesulfonyl]-2-hydroxycarbamoyl-piperidine-4-carboxylic acid methyl ester.

EXAMPLE 6

2R,3S-(1-[4-(4-Fluorobenzyloxy)-benzenesulfonyl]-2-hydroxycarbamoyl-piperidin-3-yl)-carbamic acid isopropyl ester (a) To a stirred, cold (0° C.) solution of the known (Agami, C.; Hamon, L; Kadouri-Puchot, C.; Le Guen, V J. Org. Chem. 1996, 61, 5736–5742) [4S-4α,9α,9aα]1-oxo-4-phenyl-octahydro-pyrido[2,1-c][1,4]oxazine-9-carboxylic acid methyl ester (8.28 g, 2.86 mmol) in 100 mL of tetrahydrofuran was added 2.39 mL of concentrated hydrochloric acid. After 5 minutes the mixture was concentrated to dryness. The resulting solid was suspended in ethyl acetate and the mixture was stirred for an hour. The solids were collected by filtration, rinsed with ethyl acetate, and dried to give 9.04 g of a white solid.

Two grams of this solid was dissolved in 26 mL of 6 N hydrochloric acid and heated at reflux for 6 hours. The mixture was cooled to 0° C. and neutralized with 3 N sodium hydroxide and concentrated in vacuo. The resulting solids were suspended in chloroform and passed through a 45 μm nylon filter. The filtrate was concentrated to a yellow oil which was purified by flash chromatography (eluting with 2:1 hexanes/ethyl acetate with 1% acetic acid) to give 802 mg of [4S-4α9α,9aα]1-oxo-4-phenyl-octahydro-pyrido[2,1-c][1,4]oxazine-9-carboxylic acid as white solid.

(b) To a stirred solution of [4S-4α,9α,9aα]1-oxo-4-phenyl-octahydro-pyrido[2,1-c][1,4]oxazine-9-carboxylic acid (568 mg, 2.06 mmol) in 15 mL of benzene was added triethylamine (0.28 mL, 2.06 mmol) and diphenylphosphoryl azide (0.44 mL, 2.06 mmol) at 22° C. under a nitrogen atmosphere. The mixture was stirred at 22° C. for 45 minutes and at reflux for 50 minutes before 2-propanol (3.2 mL, 41.2 mmol) was added. After an additional 20 hours at reflux the mixture was cooled to 22° C. and concentrated in vacuo. The residue was taken up in ethyl acetate and the resulting solution was washed with 5% citric acid, water, saturated aqueous sodium bicarbonate, and brine. The organic layer was dried (sodium sulfate), filtered, and the filtrate was concentrated in vacuo. The yellow residue was purified by flash chromatography (eluting with 3:1 hexanes/ethyl acetate) to give 402 mg of [4S,4α,9α,9aα](1-oxo-4-phenyl-octahydro-pyrido[2,1-c][1,4]oxazin-9-yl)-carbamic acid isopropyl ester as white solid.

(c) A mixture of [4S-4α,9α,9aα](1-oxo-4-phenyl-octahydro-pyrido[2,1-c][1,4]oxazin-9-yl)-carbamic acid isopropyl ester (900 mg, 2.71 mmol) and 20% palladium hydroxide on carbon (920 mg) in 77 mL of ethanol/water (10:1) was shaken in a Parr apparatus under a 45 psi hydrogen gas atmosphere for 72 hours. The catalyst was removed by passage of the mixture through a 0.45 μm nylon filter and the filtrate was concentrated to give 610 mg of 2R,3S-3-isopropoxycarbonylamino-piperidine-2-carboxylic acid as white solid. MS: 229 (M−1).

(d) To a stirred solution of 2R,3S-3-isopropoxy-carbonylamino-piperidine-2-carboxylic acid (320 mg, 1.39 mmol) in 5 mL of methylene chloride was added triethylamine (0.58 mL, 4.17 mmol) followed by 4-(4-fluorobenzyloxy)-benzenesulfonyl chloride (460 mg, 1.53 mmol). After 16 hours at 22° C. the mixture was partioned between 1 N hydrochloric acid and ethyl acetate. The organic layer was removed and washed with brine and dried over sodium sulfate. Filtration and concentration of the filtrate gave 480 mg of crude 2R,3S-1-[4-(4-fluorobenzyloxy)-benzenesulfonyl]-3-isopropoxycarbonylamino-piperidine-2-carboxylic acid as a light yellow solid.

(e) To a stirred, cold (0° C.) solution of crude 2R,3S-1-[4-(4-fluorobenzyloxy)-benzenesulfonyl]-3-isopropoxycarbonylamino-piperidine-2-carboxylic acid (380 mg, 0.77 mmol) in 5 mL of methylene chloride was added triethylamine (0.32 mL, 2.31 mmol) followed by benzotriazol-1-yloxy-tris(dimethylamino)phosphonium hexafluorophosphate (510 mg, 1.15 mmol). The resulting solution was stirred for 2 minutes at 0° C. under a nitrogen atmosphere before O-(trimethylsilylethyl)hydroxylamine hydrochloride (195 mg, 1.15 mmol) was added. The mixture was allowed to warm slowly to 22° C. over 14 hours. The mixture was concentrated in vacuo and the residue was diluted with water and extracted with ethyl acetate/diethyl ether (1:1; 3x). The combined organic extracts were washed with saturated aqueous carbonate (2x), water (2x), and brine (1x). The organic layer was dried (magnesium sulfate), filtered, and the filtrate was concentrated in vacuo. The yellow residue was purified by flash chromatography (eluting with 65:35 hexanes/ethyl acetate) to give 300 mg of 2R,3S,[1-[4-(4-fluorobenzyloxy)-benzenesulfonyl]-2-(2-trimethylsilanyl-ethoxycarbamoyl)-piperidin-3-yl]-carbamic acid isopropyl ester as a white foam. MS: 610 (M+1).

(f) To a stirred, cold (0° C.) solution of 2R,3S-[1-[4-(4-fluorobenzyloxy)-benzenesulfonyl]-2-(2-trimethylsilanyl-ethoxycarbamoyl)-piperidin-3-yl]-carbamic acid isopropyl ester (265 mg, 0.44 mmol) in 4 mL of methylene chloride was added 3 mL of trifluoroacetic acid. The resulting colorless solution was allowed to warm to 23° C. over 2 hours and was stirred for an additional 28 hours. The mixture was concentrated in vacuo to a solid/foam, which was suspended in ethyl acetate hexanes (1:6) and stirred for 10 hours. The while solids were collected by filtration, rinsed with hexanes, and purified further by flash chromatography (eluting with 7:3 ethyl acetate/hexanes with 1% acetic acid) to give 130 mg of 2R,3S-1-[4-(4-fluorobenzyloxy)benzenesulfonyl]-2-hydroxycarbamoyl-piperidin-3-yl)-carbamic acid isopropyl ester as a white solid/foam. MS: 510 (M+1).

EXAMPLE 7

3-(S)-4-(4'-Fluorobiphenyl-4-sulfonyl)-2,2-dimethyl-thiomorpholine-3-carboxylic acid hydroxyamide (a) To a stirred solution of the known (PCT Publication WO 97/20824) 3-(S)-dimethylthexylsilyl-2,2-dimethyltetrahydro-2H-1,4-thiazine-3-carboxylate (1.17 g, 3.70 mmol) in 6 mL of methylene chloride was added triethylamine (1.02 mL, 7.40 mmol) followed by 4'-fluorobiphenylsulfonyl chloride (1.0 g, 3.70 mmol). The resulting solution was stirred for 56 hours at 23° C. The reaction mixture was diluted with methylene chloride and washed with water. The organic layer was concentrated in vacuo; the residue was dissolved in methanol, and the mixture was heated at reflux for 6 hours. The mixture was cooled to 23° C. and concentrated in vacuo. The residue was purified by flash chromatography (eluting with 3:7 ethyl acetate/hexanes with 0.1% acetic acid) to give 570 mg of 3-(S)-4-(4'-fluorobiphenyl-4-sulfonyl)-2,2-dimethyl-thiomorpholine-3-carboxylic acid as a white foam/solid. MS: 427 (M+NH$_4$).

(b) To a stirred, cold (0° C.) solution of 3-(S)-4-(4'-fluorobiphenyl-4-sulfonyl)-2,2-dimethyl-thiomorpholine-3-carboxylic acid (605 mg, 1.48 mmol) in 5 mL of methylene chloride was added triethylamine (0.62 mL, 4.43 mmol) under a nitrogen atmosphere. Benzotriazol-1-yloxy-tris (dimethylamino)phosphonium hexafluorophosphate (980 mg, 2.22 mmol) was added and the resulting solution was stirred for 5 minutes before O-(trimethylsilylethyl) hydroxylamine hydrochloride (376 mg, 2.22 mmol) was added. The ice bath was removed and the mixture was stirred for 20 hours at 23° C. The mixture was diluted with aqueous ammonium chloride and extracted with 1:1 ethyl acetate/ diethyl ether (3x). The combined organic extracts were washed with saturated aqueous sodium carbonate (2x), water (1x), and brine (1x). The organic layer was dried (magnesium sulfate), filtered, and the filtrate was concentrated in vacuo. The residual yellow oil was purified by flash chromatography (eluting with 3:7 ethyl acetate/hexanes) to give 650 mg of 3-(S)-4-(4'-fluorobiphenyl-4-sulfonyl)-2,2-dimethyl-thiomorpholine-3-carboxylic acid (2-trimethylsilanyl-ethoxy)-amide as a white foam. MS: 623 (M−1).

(c) A solution of 3-(S)-4-(4'-fluorobiphenyl-4-sulfonyl)-2,2-dimethyl-thiomorpholine-3-carboxylic acid (2-trimethylsilanyl-ethoxy)-amide (650 mg, 1.24 mmol) in 8 mL of trifluoroacetic acid was stirred for at 22° C. for 16 hours. The mixture was concentrated in vacuo and the residue was triturated with methylene chloride and diethyl ether. The solvent was removed to give 550 mg of a tan solid. The solid was suspended in 1:1 diethyl ether/hexanes and stirred gently for 20 hours. The solids were collected by filtration (1:1 diethyl ether/hexanes rinsing) and dried to give 470 mg of 3-(S)-4-(4'-fluorobiphenyl-4-sulfonyl)-2,2-dimethyl-thiomorpholine-3-carboxylic acid hydroxyamide as white solid. MS: 423 (M−1).

EXAMPLE 8

3-(S)-4-[4-(4-Fluorobenzyloxy)benzenesulfonyl]-2,2-dimethyl-thiomorpholine-3-carboxylic acid hydroxyamide (a) To a stirred, cold (0° C.) solution of the known (Belgain Patent Publication BE 893025) 2,2-dimethyl-thiomorpholine-3-carboxylic acid (600 mg, 3.42 mmol) in 10 mL of 1:1 water/dioxane was added 6 N sodium hydroxide (1.2 mL, 7.1 mmol). To the resulting solution 4-(4-fluorobenzyloxy)benzenesulfonyl chloride (1.08 g, 3.77 mmol) was added. After 30 and 50 minutes an additional 1 gram of 4-(4-fluorobenzyloxy)benzenesulfonyl chloride and 1.2 mL of 6 N sodium hydroxide was added. The mixture (pH ca. 12) was diluted with water and extracted with diethyl ether (1x). The ethereal layer was washed with 1 N sodium hydroxide; the combined basic aqueous layers were acidified to pH 3 using concentrated hydrochloric acid, and the acidic mixture was extracted with ethyl acetate (3x). The combined organic extracts were dried (sodium sulfate), filtered, and the filtrate was concentrated in vacuo to give 820 mg of 3-(S)-4-[4-(4-fluorobenzyloxy)benzenesulfonyl]-2,2-dimethyl-thiomorpholine-3-carboxylic acid as a white solid. MS: 439 (M−1).

(b) To a stirred, cold (0° C.) solution of 3-(S)-4-[4-(4-fluorobenzyloxy)-benzenesulfonyl]-2,2-dimethyl-thiomorpholine-3-carboxylic acid (820 mg, 1.87 mmol) in 5 mL of methylene chloride was added triethylamine (0.52 mL, 3.74 mmol) under a nitrogen atmosphere. Benzotriazol-1-yloxy-tris(dimethylamino)phosphonium hexafluorophosphate (1.24 g, 2.81 mmol) was added and the resulting solution was stirred for 5 minutes before O-(tert-butyldimethylsilyl)hydroxylamine (550 mg, 3.74 mmol) was added. The ice bath was removed and the mixture was stirred for 16 hours at 23° C. The mixture was diluted with aqueous ammonium chloride and extracted with ethyl acetate (3x). The combined organic extracts were washed with water, brine and dried over sodium sulfate. Filtration and concentration of the filtrate gave a viscous yellow oil, which was purified by flash chromatography (eluting with 1:3 ethyl acetate/hexanes) to give 270 mg of 3-(S)-4-[4-(4-fluorobenzyloxy)benzenesulfonyl]-2,2-dimethyl-thiomorpholine-3-carboxylic acid (tert-butyldimethylsiloxy)-amide as a white foam. MS: 569 (M+1).

(c) To a stirred, cold (0° C.) solution of 3-(S)-4-[4-(4-fluorobenzyloxy)benzenesulfonyl]-2,2-dimethyl-thiomorpholine-3-carboxylic acid (tert-butyldimethylsiloxy)-amide (270 mg, 0.47 mmol) in 10 mL of tetrahydrofuran was added two drops of concentrated hydrochloric acid. After 30 minutes the mixture was diluted with 15 mL of tetrahydrofuran and the mixture was concentrated in vacuo to a volume of ca. 5 mL. The volume was adjusted to ca. 25 mL with tetrahydrofuran and the mixture was concentrated again to ca. 5 mL. This process was repeated twice more before the mixture was finally concentrated to dryness. The resulting solids were suspended in a mixture of hexanes and diethyl ether and the mixture was stirred for 16 hours. The solid were collected by filtration, rinsed with diethyl ether,and dried to give 180 mg of 3-(S)-4-[4-(4-fluorobenzyloxy)benzenesulfonyl]-2,2-dimethyl-thiomorpholine-3-carboxylic acid hydroxyamide as a white solid. MS: 453 (M−1). $^1$H NMR (400 MHz, dmso-d$_6$) δ 10.63 (s, 1 H), 8.80 (bs, 1 H) 7.59–7.61 (m, 2 H), 7.46–7.50 (m, 2 H), 7.17–7.21 (m, 2 H), 7.09–7.12 (m, 2 H), 5.12 (s, 2 H), 3.99 (s, 1 H), 3.87–3.93 (m, 1 H), 3.69 (d, 1 H, J=12.7 Hz), 2.78–2.86 (m, 1 H), 2.44–2.50 (m, 1 H), 1.35 (s, 3 H), 1.12 (s, 3H).

Preparation 1

4-(4-Fluorobenzyloxy)benzenesulfonyl chloride

To a stirred solution of 4-hydroxybenzenesulfonic acid sodium salt dihydrate (5.13 g, 22.1 mmol) in 23 mL of 1 N sodium hydroxide was added a solution of 4-fluorobenzyl bromide (3.3 mL, 26.5 mmol) in 20 mL of ethanol. The mixture was heated at reflux for two days, then cooled to ambient temperature (22° C.), whereupon a white precipitate formed. The flaky white solids were collected by filtration, rinsed with ethyl acetate and diethyl ether, and dried to give 4.95 g of 4-(4-fluoro-benzyloxy)-benzenesulfonic acid sodium salt. A stirred solution of 4-(4-fluoro-benzyloxy)- benzenesulfonic acid sodium salt (13.0 g, 42.7 mmol) in 50 mL of thionyl chloride and two drops of dimethylformamide was heated at a gentle reflux for 8 hours. The mixture was concentrated to a yellow solid which was suspended in ethyl acetate and filtered. The filtrate was concentrated to 11.2 g of 4-(4-fluorobenzyloxy)benzenesulfonyl chloride as a light yellow solid: $^1$H NMR (400 MHz, CDCl$_3$) δ 7.95–7.98 (m, 2 H), 7.38–7.41 (m, 2 H), 7.06–7.12 (m, 4 H), 5.12 (s, 2 H).

Preparation 2

3-(4-Fluorophenoxy)-propane-1-sulfonyl chloride

To a stirred solution of 4-fluorophenol (5.0 g, 44.6 mmol) in 50 mL of toluene was added sodium hydride (60% dispersion in mineral oil, 1.78 g, 44.6 mmol) at ambient temperature (22° C.). After 20 minutes, a solution of 1,3-propane sulfone (3.9 mL, 44.6 mmol) in toluene was added slowly and the mixture was stirred for 16 hours. The reaction was quenched by the addition of methanol and the mixture was concentrated in vacuo to an off-white solid. This solid was suspended in ethyl acetate, filtered, and the solids were collected and dried to give 10.9 g of 3-(4-fluorophenoxy)-propane-1-sulfonic acid sodium salt as an off-white powder. A stirred solution of 3-(4-fluorophenoxy)-propane-1-sulfonic acid sodium salt (2.0 g, 7.8 mmol) in 10 mL of thionyl chloride and one drops of dimethylformamide was heated at reflux for 16 hours. The mixture was then cooled to 0° C., diluted with 25 mL of diethyl ether, and the reaction was quenched by the slow addition of water. The organic layer was removed and the aqueous layer was extracted with 25 mL of diethyl ether. The combined organic layers were washed with brine and dried over sodium sulfate. Filtration and concentration gave 1.75 g of 3-(4-fluoro-phenoxy)-propane-1-sulfonyl chloride as a yellow oil: $^1$H NMR (400 MHz, CDCl$_3$) δ 6.96–7.00 (m, 2 H), 6.80–6.84 (m, 2 H), 4.10 (t, 2 H, J=5.5 Hz), 3.91 (t, 2 H, J=7.5 Hz) 2.47–2.54 (m, 2 H).

Preparation 3

4'-Fluorobiphenylsulfonyl chloride

Chlorosulfonic acid (8.7 mL, 0.13 mole) was added dropwise to stirred cold (0° C.) 4-fluorobiphenyl (10.2 g, 59 mmol). After 30 minutes at 0° C. the reaction mixture was poured onto ice. The resulting white precipitate was collected by filtration and dissolved in chloroform. The chloroform solution was washed with water, brine, dried over magnesium sulfate, and concentrated to afford a white solid. The desired 4'-fluorobiphenylsulfonyl chloride (4.3 g), was separated from 4'-fluorobiphenylsulfonic acid by crystallization of the latter from ethyl acetate and crystallization of the remaining material from hexanes.

What is claimed is:

1. A compound of the formula

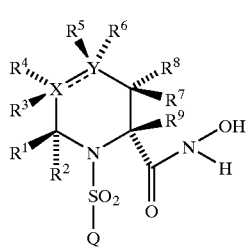

I or the pharmaceutically acceptable salt thereof, wherein the broken line represents an optional double bond;

X is carbon;

Y is carbon;

$R^1$, $R^2$, $R^3$, $R^4$, $R^5$, $R^6$, $R^7$, $R^8$ and $R^9$ are selected from the group consisting of hydrogen, $(C_1-C_6)$alkyl optionally substituted by one or two groups selected from $(C_1-C_6)$alkylthio, $(C_1-C_6)$alkoxy, trifluoromethyl, halo, $(C_6-C_{10})$aryl, $(C_5-C_9)$heteroaryl, $(C_6-C_{10})$arylamino, $(C_6-C_{10})$arythio, $(C_6-C_{10})$aryloxy, $(C_5-C_9)$heteroarylamino, $(C_5-C_9)$heteroarylthio, $(C_5-C_9)$heteroaryloxy, $(C_6-C_{10})$aryl$(C_6-C_{10})$aryl, $(C_3-C_6)$cycloalkyl, hydroxy, piperazinyl, $(C_6-C_{10})$aryl$(C_1-C_6)$alkoxy, $(C_5-C_9)$heteroaryl$(C_1-C_6)$alkoxy, $(C_1-C_6)$acylamino, $(C_1-C_6)$acylthio, $(C_1-C_6)$acyloxy, $(C_1-C_6)$alkylsulfinyl, $(C_6-C_{10})$arylsulfinyl, $(C_1-C_6)$alkylsulfonyl, $(C_6-C_{10})$arylsulfonyl, amino, $(C_1-C_6)$alkylamino or $(C_1-C_6)$alkylamino)$_2$; $(C_2-C_6)$alkenyl, $(C_6-C_{10})$aryl$(C_2-C_6)$alkenyl, $(C_5-C_9)$heteroaryl$(C_2-C_6)$alkenyl, $(C_2-C_6)$alkynyl, $(C_6-C_{10})$aryl$((C_2-C_6)$alkynyl, $(C_5-C_9)$heteroaryl$((C_2-C_6)$alkynyl, $(C_1-C_6)$alkylamino, $(C_1-C_6)$alkylthio, $(C_1-C_6)$alkoxy, perfluoro$(C_1-C_6)$alkyl, $(C_6-C_{10})$aryl, $(C_5-C_9)$heteroaryl, $(C_6-C_{10})$arylamino, $(C_6-C_{10})$arylthio, $(C_6-C_{10})$aryloxy, $(C_5-C_9)$heteroarylamino, $(C_5-C_9)$heteroarylthio, $(C_5-C_9)$heteroaryloxy, $(C_3-C_6)$cycloalkyl, $(C_1-C_6)$alkyl(hydroxymethylene), piperidyl, $(C_1-C_6)$alkylpiperidyl, $(C_1-C_6)$acylamino, $(C_1-C_6)$acylthio, $(C_1-C_6)$acyloxy, $R^{10}(C_1-C_6)$alkyl wherein $R^{10}$ is $(C_1-C_6)$acylpiperazino, $(C_6-C_{10})$arylpiperazino, $(C_5-C_9)$heteroarylpiperazino, $(C_1-C_6)$alkylpiperazino, $(C_6-C_{10})$aryl$(C_1-C_6)$alkylpiperazino, $(C_5-C_9)$heteroaryl$(C_1-C_6)$alkylpiperazino, morpholino, thiomorpholino, pyrrolidino, piperidyl, $(C_1-C_6)$alkylpiperidyl, $(C_6-C_{10})$arylpiperidyl, $(C_5-C_9)$heteroarylpiperidyl, $(C_1-C_6)$alkylpiperidyl$(C_1-C_6)$alkyl, $(C_6-C_{10})$arylpiperidyl$(C_1-C_6)$alkyl, $(C_5-C_9)$heteroarylpiperidyl$(C_1-C_6)$alkyl or $(C_1-C_6)$acylpiperidyl;

or a group of the formula

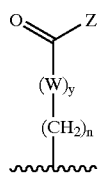

II wherein n is 0 to 6;

y is 0 or 1;

W is oxygen or $NR^{24}$ wherein $R^{24}$ is hydrogen or $(C_1-C_6)$alkyl;

Z is $OR^{11}$ or $NR^{24}R^{11}$ wherein $R^{24}$ is as defined above and $R^{11}$ is as defined below; azetidinyl, pyrrolidinyl, piperidinyl, piperazinyl, morpholinyl, thiomorpholinyl, indolinyl, isoindolinyl, tetrahydroquinolinyl, tetrahydroisoquinolinyl or a bridge diazabicycloalkyl ring selected from the group consisting of

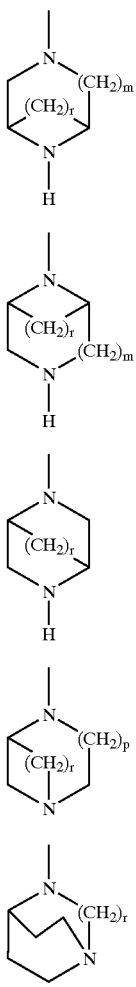

wherein r is 1, 2 or 3;
m is 1 or 2;
p is 0 or 1; and
wherein each heterocyclic group may optionally be substituted by one or two groups selected from hydroxy, $(C_1-C_6)$alkyl, $(C_1-C_6)$alkoxy, $(C_1-C_{10})$acyl, $(C_1-C_{10})$acyloxy, $(C_6-C_{10})$aryl, $(C_5-C_9)$heteroaryl, $(C_6-C_{10})$aryl$(C_1-C_6)$alkyl, $(C_5-C_9)$heteroaryl$(C_1-C_6)$alkyl, hydroxy$(C_1-C_6)$alkyl, $(C_1-C_6)$alkoxy$(C_1-C_6)$alkyl, $(C_1-C_6)$acyloxy$(C_1-C_6)$alkyl, $(C_1-C_6)$alkylthio, $(C_1-C_6)$alkylthio$(C_1-C_6)$alkyl, $(C_6-C_{10})$arylthio, $(C_6-C_{10})$arylthio$(C_1-C_6)$alkyl, $R^{12}R^{13}N$, $R^{12}R^{13}NSO_2$, $R^{12}R^{13}NCO$, $R^{12}R^{13}NCO(C_1-C_6)$alkyl wherein $R^{12}$ and $R^{13}$ are each independently hydrogen, $(C_1-C_6)$alkyl, $(C_6-C_{10})$aryl, $(C_5-C_9)$heteroaryl, $(C_6-C_{10})$aryl $(C_1-C_6)$alkyl or $(C_5-C_9)$heteroaryl$(C_1-C_6)$alkyl or $R^{12}$ or $R^{13}$ may be taken together with the nitrogen to which they are attached to form an azetidinyl, pyrrolidinyl, piperidinyl, morpholinyl or thiomorpholinyl ring; $R^{14}SO_2$, $R^{14}SO_2NH$ wherein $R^{14}$ is trifluoromethyl, $(C_1-C_6)$alkyl, $(C_6-C_{10})$aryl, $(C_5-C_9)$heteroaryl, $(C_6-C_{10})$aryl$(C_1-C_6)$alkyl or $(C_5-C_9)$heteroaryl $(C_1-C_6)$alkyl; $R^{15}CONR^{12}$ wherein $R^{12}$ is as defined above and $R^{15}$ is hydrogen, $(C_1-C_6)$alkyl, $(C_1-C_6)$alkoxy, $(C_6-C_{10})$aryl, $(C_5-C_9)$heteroaryl, $(C_1-C_6)$aryl$(C_1-C_6)$alkyl$(C_6-C_{10})$aryl$(C_1-C_6)$alkoxy or $(C_5-C_9)$heteroaryl$(C_1-C_6)$alkyl;
$R^{16}OOC$, $R^{16}OOC(C_1-C_6)$alkyl wherein $R^{16}$ is $(C_1-C_6)$alkyl, $(C_6-C_{10})$aryl, $(C_5-C_9)$heteroaryl, $(C_6-C_{10})$aryl$(C_1-C_6)$alkyl, 5-indanyl, $CHR^{17}OCOR^{18}$ wherein $R^{17}$ is hydrogen or $(C_1-C_6)$alkyl and $R^{18}$ is $(C_1-C_6)$alkyl, $(C_1-C_6)$alkoxy or $(C_6-C_{10})$aryl; $CH_2CONR^{19}R^{20}$ wherein $R^{19}$ and $R^{20}$ are each independently hydrogen or $(C_1-C_6)$alkyl or may be taken together with the nitrogen to which they are attached to form an azetidinyl, pyrrolidinyl, piperidinyl, morpholinyl or thiomopholinyl ring; or $R^{21}O$ $(C_1-C_6)$alkyl wherein $R^{21}$ is $H_2N(CHR^{22})CO$ wherein $R^{22}$ is the side chain of a natural D- or L-amino acid;

$R^{11}$ is hydrogen, $(C_6-C_{10})$aryl, $(C_5-C_9)$heteroaryl, $(C_6-C_{10})$aryl$(C_1-C_6)$alkyl, $(C_5-C_9)$heteroaryl$(C_1-C_6)$alkyl, $(C_1-C_6)$alkyl$(C_6-C_{10})$aryl$(C_1-C_6)$alkyl, $(C_1-C_6)$alkyl$(C_5-C_9)$heteroaryl$(C_1-C_6)$alkyl, 5-indanyl, $CHR^{17}OCOR^{18}$ or $CH_2CONR^{19}R^{20}$ wherein $R^{17}$, $R^{18}$, $R^{19}$ and $R^{20}$ are as defined above;

or $R^1$ and $R^2$, or $R^3$ and $R^4$, or $R^5$ and $R^6$ may be taken together to form a carbonyl; and Q is $(C_1-C_{10})$alkyl, $(C_6-C_{10})$aryl, $(C_6-C_{10})$aryloxy$(C_6-C_{10})$aryl, $(C_6-C_{10})$aryl$(C_6-C_{10})$aryl, $(C_6-C_{10})$aryl$(C_6-C_{10})$aryl$(C_1-C_6)$alkyl, $(C_6-C_{10})$aryl$(C_1-C_6)$alkoxy$(C_1-C_6)$alkyl, $(C_6-C_{10})$aryloxy$(C_5-C_9)$heteroaryl, $(C_5-C_9)$heteroaryl, $(C_1-C_6)$alkyl$(C_6-C_{10})$aryl, $(C_1-C_6)$alkoxy$(C_6-C_{10})$aryl, $(C_6-C_{10})$aryl$(C_1-C_6)$alkoxy$(C_6-C_{10})$aryl, $(C_5-C_9)$heteroaryloxy$(C_6-C_{10})$aryl, $(C_1-C_6)$alkyl$(C_5-C_9)$heteroaryl, $(C_1-C_6)$alkoxy$(C_5-C_9)$heteroaryl, $(C_6-C_{10})$aryl$(C_1-C_6)$alkoxy$(C_5-C_9)$heteroaryl, $(C_5-C_9)$heteroaryloxy$(C_5-C_9)$heteroaryl, $(C_6-C_{10})$aryloxy$(C_1-C_6)$alkyl, $(C_5-C_9)$heteroaryloxy$(C_1-C_6)$alkyl, $(C_1-C_6)$alkyl$(C_6-C_{10})$aryloxy$(C_6-C_{10})$aryl, $(C_1-C_6)$alkyl$(C_5-C_9)$heteroaryloxy$(C_6-C_{10})$aryl, $(C_1-C_6)$alkyl$(C_6-C_{10})$aryloxy$(C_5-C_9)$heteroaryl, $(C_1-C_6)$alkoxy$(C_6-C_{10})$aryloxy$(C_6-C_{10})$aryl, $(C_1-C_6)$alkoxy$(C_5-C_9)$heteroaryloxy$(C_6-C_{10})$aryl or $(C_1-C_6)$alkoxy$(C_6-C_{10})$aryloxy$(C_5-C_9)$heteroaryl optionally substituted by fluoro, chloro, $(C_1-C_6)$alkyl, $(C_1-C_6)$alkoxy or perfluoro$(C_1-C_3)$alkyl;

with the proviso that Z must be substituted when defined as azetidinyl, pyrrolidinyl, morpholinyl, thiomorpholinyl, indolinyl, isoindolinyl, tetrahydroquinolinyl, tetrahydroisoquinolinyl, piperazinyl, $(C_1-C_{10})$acylpiperazinyl, $(C_1-C_6)$alkylpiperazinyl, $(C_6-C_{10})$arylpiperazinyl, $(C_5-C_9)$heteroarylpiperazinyl or a bridged diazabicycloalkyl ring;

with the proviso that $R^7$ is other than hydrogen only when $R^8$ is other than hydrogen;

with the proviso that $R^6$ is other than hydrogen only when $R^5$ is other than hydrogen;

with the proviso that $R^3$ is other than hydrogen only when $R^4$ is other than hydrogen;

with the proviso that $R^2$ is other than hydrogen only when $R^1$ is other than hydrogen;

with the proviso that when $R^1$, $R^2$ and $R^9$ are a substitute containing a heteroatom, the heteroatom cannot be directly bonded to the 2- or 6-positions;

with the proviso that when y is 1 and W is $NR^{24}$ or oxygen, Z cannot be hydroxy;

with the proviso that when Y is oxygen, sulfur, SO or $SO_2$, $R^5$ and $R^6$ are not present;

with the proviso that when Y is nitrogen, $R^6$ is not present;

with the proviso that when the broken line represents a double bond, $R^4$ and $R^6$ are not present;

with the proviso that when $R^3$ and $R^5$ are independently a substituent containing a heteroatom when the broken line represents a double bond, the heteroatom cannot be directly bonded to positions X and Y;

with the proviso that at least one of $R^1$, $R^2$, $R^3$, $R^4$, $R^5$, $R^6$, $R^7$, $R^8$ and $R^9$ must be defined as the group of formula II.

2. A compound of claim 1, wherein Q is $(C_1-C_6)$alkoxy$(C_6-C_{10})$aryl, $(C_6-C_{10})$aryl$(C_1-C_6)$alkoxy$(C_6-C_{10})$aryl, or $(C_6-C_{10})$aryl$(C_1-C_6)$alkoxy$(C_1-C_6)$alkyl wherein each terminal aryl group is optionally substituted by fluoro.

3. A compound of claim 1 wherein Q is $(C_1-C_6)$alkoxy$(C_6-C_{10})$aryl, $(C_6-C_{10})$aryl$(C_1-C_6)$alkoxy$(C_6-C_{10})$aryl, or $(C_6-C_{10})$aryl$(C_1-C_6)$alkoxy$(C_1-C_6)$alkyl.

4. A compound of claim 1 selected from the group consisting of:

(2R,4)-1-[4-(4-Fluorobenzyloxy)-benzenesulfonyl]-2-hydroxycarbamoyl-piperidine-4-carboxylic acid; and (2R,4R)-1-(4-Methoxybenzenesulfonyl)-4-(piperidine-1-carbonyl)-piperidine-2-carboxylic acid hydroxyamide hydrochloride.

5. A compound of claim 1 selected from the group consisting of:

(2R,4R)-1-[3-(4-Fluorophenoxy)-propane-1-sulfonyl]-2-hydroxycarbamoyl-piperidine-4-carboxylic acid methyl ester;

(2R,4R)-1-[3-(4-Fluorophenoxy)-propane-1-sulfonyl]-2-hydroxycarbamoyl-piperidine-4-carboxylic acid;

(2R,4R)-1-[4-(4-Fluorobenzyloxy)-benzenesulfonyl]-2-hydroxycarbamoyl-piperidine-4-carboxylic acid methyl ester;

(2R,4R)-1-[4-(4-Fluorobenzyloxy)-benzenesulfonyl]-2-hydroxycarbamoyl-piperidine-4-carboxylic acid; and (2R,3S)-{1-[4-(4-Fluorobenzyloxy)-benzenesulfonyl]-2-hydroxycarbamoyl-piperidin-3-yl}-carbamic acid isopropyl ester.

6. A pharmaceutical composition comprising a compound of claim 1 and a pharmaceutically acceptable carrier.

7. A method for the inhibition of (a) matrix metalloproteinases or (b) the production of tumor necrosis factor (TNF) in a mammal in need of inhibition of matrix metalloproteinases or the production of TNF comprising administering to said mammal an effective amount of a compound of claim 1 or a pharmaceutically acceptable salt thereof.

8. A method according to claim 7 wherein said mammal is a human.

* * * * *